United States Patent [19]

Chang

[11] Patent Number: 4,846,875

[45] Date of Patent: Jul. 11, 1989

[54] HERBICIDAL TRIAZOLINONES

[75] Inventor: Jun H. Chang, Princeton Junction, N.J.

[73] Assignee: FMC Corporation, Philadelphia, Pa.

[21] Appl. No.: 76,110

[22] Filed: Jul. 21, 1987

[51] Int. Cl.$^4$ .................. A01N 43/653; C07D 249/10
[52] U.S. Cl. ........................ 71/92; 548/265; 548/225; 544/96; 540/488
[58] Field of Search ............. 548/265, 263; 71/92

[56] References Cited

U.S. PATENT DOCUMENTS

| | | | |
|---|---|---|---|
| 4,213,773 | 7/1980 | Wolf | 71/92 |
| 4,318,731 | 3/1982 | Kajioka et al. | 71/92 |
| 4,404,019 | 9/1983 | Uematsu et al. | 71/92 |

FOREIGN PATENT DOCUMENTS

| | | | |
|---|---|---|---|
| 0053662 | 5/1981 | Japan | 548/263 |
| 58-225070 | 12/1983 | Japan | 71/92 |
| 85/01637 | 4/1985 | PCT Int'l Appl. | 71/92 |
| 85/04307 | 10/1985 | PCT Int'l Appl. | 71/92 |
| 86/02642 | 5/1986 | PCT Int'l Appl. | 71/92 |
| 87/00730 | 2/1987 | PCT Int'l Appl. | 71/92 |
| 2090250 | 7/1982 | United Kingdom | 71/92 |

OTHER PUBLICATIONS

Derwent Abstract 84-034252/06, English language abstract of Japan 58-225,070, reference E above.

*Primary Examiner*—Robert T. Bond
*Attorney, Agent, or Firm*—Robert M. Kennedy; H. Robinson Ertelt; Beverly K. Johnson

[57] ABSTRACT

A herbicidal compound which is a Q-substituted 1-aryl-4,5-dihydro-1,2,4-triazol-5(1H)-one in which the Q-substituent is on the ring-carbon atom at the 5-position of the aryl group and in which: Q is (a) —CH($R^1$)ZR in which Z is O or S(O)$_n$ and n is zero, one or two; or (b) —CH($R^1$)N($R^4$)($R^5$); or (c) —C($R^9$)=N$R^6$; or (d) —CHO$R^7$C(O)N$R^8$.

4 Claims, No Drawings

HERBICIDAL TRIAZOLINONES

This invention relates to herbicidal 1-aryl-4,5-dihydro-1,2,4-triazol-5(1H)-ones.

The herbicidal activity of certain 1-aryl-4,5-dihydro-1,2,4-triazol-5(1H)-ones (also known as 1-aryl-Δ²-1,2,4-triazolin-5-ones) has been described in the patent literature, as discussed below.

British published patent application No. 2,090,250 discloses herbicidal compounds of the formula

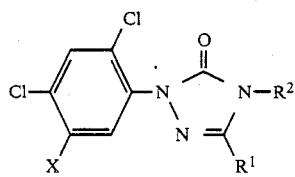

wherein $R^1$ is an alkyl group, $R^2$ is an alkynyl group, a halomethyl group, or a haloethyl group and X is an alkoxy group, an alkenyloxy group, an alkoxyalkoxy group, an alkynyloxy group, a hydroxy group, a halomethyloxy group or a haloethyloxy group.

Japanese Kokai No. 58 225070 discloses herbicidal compounds of the formula

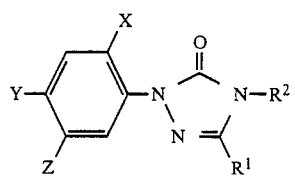

wherein $R^1$ is 1–4C alkyl; $R^2$ is H, 1–4C alkyl, halomethyl or 3–4C alkynyl; X is Cl or F; Y is Cl, Br, OH or $OR^3$; $R^3$ is 1–4C alkyl or benzyl; Z is H, carboxy, cyanomethoxy, $COOR^4$, $COSR^5$ or $CON(R^6)(R^7)$; $R^4$ is 1–4C alkyl or 3–4C alkoxyalkyl; $R^5$ is 1–4C alkyl; and $R^6$ and $R^7$ are H, 1–4C alkyl or alkoxy.

U.S. Pat. No. 4,318,731 discloses herbicidal compounds of the formula

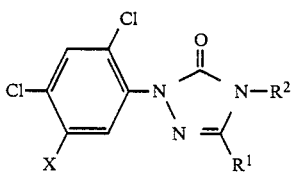

wherein $R^1$ is $C_1$–$C_4$ alkyl $R^2$ is hydrogen, $C_1$–$C_6$ alkyl or $C_1$–$C_4$ alkenyl; and X is hydroxy, $C_1$–$C_4$ alkyl, $C_1$–$C_6$ alkyloxy, an alkyloxyalkyloxy of which two alkyls may be the same or different and each alkyl is $C_1$–$C_4$, a $C_2$–$C_4$ alkenyloxy, or an alkyloxycarbonylalkyloxy of which two alkyls may be the same or different and each alkyl is $C_1$–$C_4$.

U.S. Pat. No. 4,404,019 discloses herbicidal compounds of the formula

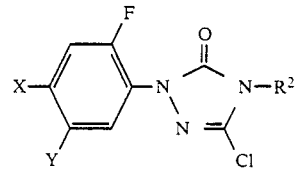

wherein R is a $C_1$–$C_4$ alkyl group, a $C_3$–$C_4$ alkenyl group or a $C_3$–$C_4$ cycloalkyl group, X is a chlorine or bromine atom and Y is a hydrogen atom or a $C_1$–$C_4$ alkoxy group.

U.S. Pat. No. 4,213,773 discloses fused ring 1,2,4-triazolin-5-ones of the formula

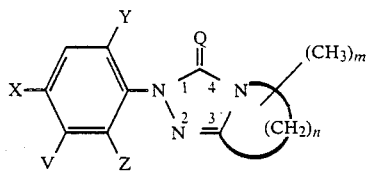

in which V may be 3–6C alkynyloxy, X is F, Cl, Br, CN, $CH_3$, $CH_3O$ or $NO_2$, Y is H, F, Cl, Br or $CH_3$, Z is H, F, Cl or Br, n is 3 to 5, m is 0–2 and Q is O or S.

PCT International Applications Nos. WO 85/01637 published Apr. 25, 1985, WO 85/0430 published Oct. 10, 1985, WO 86/04481 published Aug. 14, 1986, WO 86/02642 published May 9, 1986, and WO 87/00730 published Feb. 12, 1987 disclose various other substituted aryl-1,2,4-triazolin-5-ones in which the substituents at the 5-position of the benzene ring of the aryl group are, for instance, alkoxy, alkynyloxy, alkenyloxy, tetrahydrofuranyloxy or similar heterocycleoxy, a group of the formula $OR^3COOR^4$ (where $R^3$ may be alkylene or haloalkylene and $R^4$ may be substituted alkyl, alkenyl, etc.), alkyl, cyanoalkyl, $COR^6$ or $CH_2COR^6$ (where $R^6$ is, for instance, alkoxy or alkyl-substituted amino).

The compounds of this invention are herbicidal aryl-4,5-dihydro-1,2,4-triazol-5(1H)-ones (such as those in the prior art, e.g. the references mentioned above) in which, however, the carbon atom at the 5-position of the benzene ring carries a substituent (Q) as described below:

Q is:
(a) —$CH(R^1)ZR$ in which Z is O or $S(O)_n$ and n is zero, one or two; or
(b) —$CH(R^1)N(R^4)(R^5)$; or
(c) —$C(R^9)$=$NR^6$; or

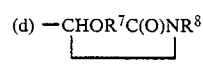

R may be:
hydrogen;
alkyl such as lower alkyl (e.g. methyl, ethyl, propyl, isopropyl, butyl or t-butyl);
haloalkyl such as halo lower alkyl (e.g. chloroethyl, fluoroethyl or fluoropropyl);
cycloalkyl (e.g. cyclohexyl, cyclopentyl or cyclopropylmethyl);
alkenyl such as lower alkenyl (e.g. allyl);
alkynyl such as lower alkynyl (e.g. propargyl);
alkoxyalkyl such as lower alkoxyalkyl (e.g. methoxymethyl or methoxyethyl);

cyclic oxyalkylene such as tetrahydropyran-2-yl or tetrahydrofuran-3-yl;

acyl such as alkylcarbonyl or haloalkylcarbonyl (e.g. —C(O)CH$_3$ or —C(O)CH$_2$F or —C(O)CH$_2$CH$_2$Cl);

alkyloxycarbonylalkyl (e.g. —CH$_2$CO$_2$C$_2$H$_5$);

aryloxycarbonylalkyl (e.g. phenoxycarbonylmethyl in which the phenoxy may be unsubstituted or may be substituted with, e.g., halo, alkoxy, alkyl or haloalkyl);

nitro;

aryl (e.g. phenyl or halo- or alkoxy- or alkyl- or haloalkyl-substituted phenyl);

aralkyl (e.g. benzyl); or cyano;

R$^1$ may be hydrogen, lower alkyl (e.g. methyl) or haloalkyl (e.g. CH$_2$Cl or CF$_3$);

R$^4$ and R$^5$ may each, independently, be:

hydrogen; alkyl such as lower alkyl (e.g. methyl, ethyl, propyl, isopropyl, butyl or t-butyl);

cycloalkyl (e.g. cyclohexyl, cyclopentyl, or cyclopropylmethyl);

alkenyl such as lower alkenyl (e.g. allyl);

alkynyl such as lower alkynyl (e.g. propargyl);

alkoxy such as methoxy;

alkoxycarbonyl such as ethoxycarbonyl;

alkoxycarbonylalkyl such as —CH(CH$_3$)CO$_2$C$_2$H$_5$;

alkylcarbonyl or haloalkylcarbonyl or alkenylcarbonyl such as methylcarbonyl, isopropylcarbonyl, mono-, di- or tri-fluoromethylcarbonyl, chloromethylcarbonyl, chloro-t-butylcarbonyl or vinylcarbonyl;

alkylaminocarbonyl such as methylaminocarbonyl;

alkylsulfonyl or haloalkylsulfonyl or arylsulfonyl such as methylsulfonyl, trifluoromethylsulfonyl, chlorophenylsulfonyl, methoxyphenylsulfonyl, methoxycarbonylphenylsulfonyl; or a substituted alkyl group such as

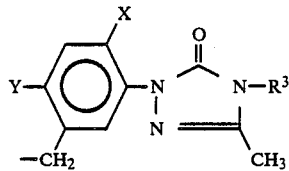

in which X, Y and R$^3$ are as defined below, as in compounds 46–49 of Table 1; or R$^4$ and R$^5$ may together constitute a divalent group such as:

an alkylene or oxa-alkylene group (e.g. —CH$_2$(CH$_2$)$_n$CH$_2$- and n=2 or 3, or —CH$_2$CH$_2$—O—CH$_2$CH$_2$—); or a group of the formula —C(O)R$^7$O—; or a di-acyl radical of a dicarboxylic acid (e.g. a phthaloyl radical as in compound 45);

R$^6$ may be:

hydroxy;

alkoxy (e.g. methoxy or ethoxy);

alkenyloxy (e.g. allyloxy);

alkynyloxy (e.g. propargyloxy);

acyloxy such as alkylcarbonyloxy (e.g. acetoxy); or trialkylsilyloxy (e.g. isopropyl dimethyl silyloxy);

R$^7$ may be alkylene (e.g. ethylene, propylene, or alkyl-substituted ethylene), which may be alkoxy-substituted or alkylthio-substituted (as in compound 33 of Table 1).

R$^8$ may be hydrogen, alkyl or alkenyl; and

R$^9$ may be hydrogen or methyl.

The other substituents on the herbicidal aryl-4,5-dihydro-1,2,4-triazol-5(1H)-ones of this invention may, for instance, be any of those present in the herbicidal aryl triazolinones of the prior art mentioned above. For instance those other substituents are so chosen that the 5-Methoxy and 5-Propargyloxy Analogs of the compounds of this invention are herbicides; the 5-Methoxy Analog of a compound of this invention has a formula which is identical with that of the compound of this invention in all respects except that the ring-carbon atom at the 5-position of the benzene ring carries a methoxy substituent instead of a substituent Q as defined above. Similarly, the 5-Propargyloxy Analog is otherwise identical except that the carbon at the 5-position of its benzene ring carries a propargyloxy substituent instead of a substituent Q as defined above. Thus the 5-Methoxy Analog of compound no. 52 of Table 1 below is 1-(4-chloro-2-fluoro-5-methoxyphenyl)-4-difluoromethyl-4,5-dihydro-3-methyl-1,2,4-triazol-5(H)-one and the 5-Propargyloxy Analog of compound no. 52 is 1-(4-chloro-2-fluoro-5-propargyloxyphenyl)-4-difluoromethyl-4,5-dihydro-3-methyl-1,2,4-triazol-5(H)-one.

The compounds of this invention preferably have 5-Methoxy Analogs and 5-Propargyloxy Analogs of marked herbicidal properties. For instance, said Analogs of the preferred compounds show at least 50% kill of at least one of the following species of plants when applied under at least one of the following modes at the rate of 0.5 kg/ha, and more preferably show such kill of at least 50% when applied at the rate of 0.1 kg/ha: Species; velvetleaf (*Abutilon theophrasti*) green foxtail (*Setaria viridis*); Modes: preemergent, postemergent. Testing for such herbicidal activity may be carried out in the manner described below under the heading "Herbicidal Activity".

Representative compounds of this invention are listed in Table 1 below.

One may describe many of the compounds of this invention by the formula

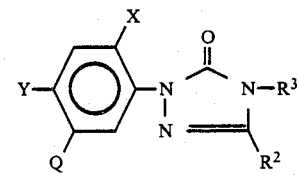

(Formula I)

in which Q has the meaning set forth above and the substituents R$^2$ and R$^3$ on the triazolinone ring may be any of those known in the literature discussed above. For instance, each may, independently, be lower alkyl (preferably methyl) or halo lower alkyl (such as fluoro lower alkyl (preferably CHF$_2$). R$^2$ may also be a halogen atom such as chlorine. The substituent X may be hydrogen; halogen such as chlorine, bromine, or fluorine (preferably fluorine); alkyl such as lower alkyl (e.g. methyl); haloalkyl such as halo lower alkyl (e.g. CF$_3$, CH$_2$F or CHF$_2$); alkoxy such as lower alkoxy (e.g. methoxy); or nitro; and Y may be hydrogen; halogen such as chlorine, bromine, or fluorine (preferably bromine or chlorine); alkyl such as lower alkyl (e.g. methyl); alkoxy such as lower alkoxy (e.g. methoxy); haloalkyl such as halo lower alkyl (e.g. fluoroalkyl); halo lower alkylsulfinyl (e.g. —SOCF$_3$); or halo lower alkoxy (e.g. —OCHF$_2$). Presently preferred X, Y substituents are: 2-F, 4-Cl; 2-F, 4-Br; 2,4-Cl; 2-Br, 4-Cl; and 2-F, 4-CF$_3$.

In each aspect of the invention it is often preferable that any alkyl, alkenyl, alkynyl or alkylene moiety (such as the hydrocarbon moiety of an alkoxy or haloalkoxy group) have less than 6 carbon atoms, e.g. 1 to 3 or 4 carbon atoms.

Any acidic compound of this invention (e.g. a sulfonamide, such as compound 8 of Table 1) may be converted into a salt such as a sodium, potassium, calcium, ammonium, magnesium, or mono-, di- or tri($C_1$ to $C_4$ alkyl)ammonium or sulfonium or sulfoxonium salt which may also be used as an herbicide.

The present compounds may be prepared by methods described in the literature or in the following Examples or by methods analogous and similar thereto and within the skill of the art.

In Example 1 a nitrotoluene is converted to the corresponding toluidine which is then converted, by known methods (such as those shown in the above-cited patent literature) to a 5-methylphenyl triazolinone; the latter is then treated (e.g. with N-bromosuccinimide) to convert it to the corresponding 5-bromomethyl compound.

The 5-bromomethyl compound may then be reacted with an appropriate primary or secondary amine (as in Examples 2 and 3) or with a primary or secondary amide (or a lactam or imide) (as in Examples 5 and 9) to produce the substituted aminomethyl compound. The latter may then be treated (e.g. if it has a hydrogen on the aminomethyl nitrogen) to introduce an additional substituent on the nitrogen, as by the acylation illustrated in Example 4. The 5-bromomethyl compound may be converted to the corresponding 5-aminomethyl compound (as by the method illustrated in Example 10 or, more simply, by treatment with $NH_3$) which may then be treated to introduce substituents on the amino group (as in Example 11).

The 5-bromomethyl compound may be treated with a nucleophile, such as an etherifying agent such as an alkali metal alkoxide or haloalkoxide (as in Example 13) or thiolate (as in Example 15) or an esterifying agent (as in Example 14 Step A). It may be converted to a 5-hydroxymethyl compound (as in Example 14 Steps A and B or by treatment with sodium hydroxide) and then etherified (as in Example 14 Step C) or esterified. The thioethers may be oxidized (as in Example 16) to form the compounds having —S(O)— or —S(O)$_2$— linkages.

Example 17, in which $R^1$ is alkyl, illustrates a process in which there is formed a substituted benzaldehyde, e.g., of the formula

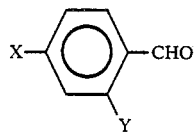

which is converted in known manner (e.g., in a series of reactions involving a Grignard reagent) to the corresponding secondary alcohol, e.g.,

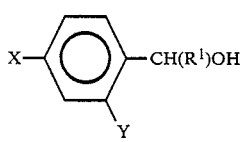

Nitration of the alcohol (under mild conditions, such as with $HNO_3$ in a solvent at a temperature of about −20 to 5° C.) before the reaction with the nucleophile not only places an $NO_2$ group on the aromatic ring but also converts the alcoholic OH group to an —$ONO_2$ group, forming, e.g.

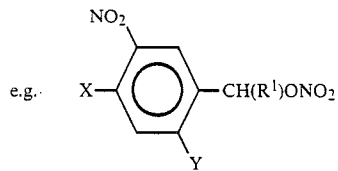

The —$ONO_2$ group may then be converted to, e.g., an OR group by reaction with a nucleophile such as a conventional etherifying agent, e.g., an alkali metal alkoxide, after which the $NO_2$ group on the benzene ring is reduced to form an amino group. The amino group may then be converted to the triazolinone group in known manner.

Compounds in which Q is $C(R^9)=NR^6$ may be made as in Example 12, in which the 5-methylphenyl compound is converted to the corresponding aldehyde (i.e. 5-formylphenyl compound) or ketone, as by dibromination to form a 5-dibromomethyl group followed by hydrolysis, after which aldehyde or ketone is reacted with hydroxylamine to form the $C(R^9)=NOH$ group, in which $R^6$ is hydroxy, (as in compound 81 of Table 1 below) or with an alkoxyamine to form a compound in which $R^6$ is alkoxy (as in compound 82). The compound in which $R^6$ is hydroxy may then be reacted with a trialkyl silyl chloride to produce a compound in which $R^6$ is trialkylsilyloxy (e.g. compound 84 made by reaction with t-butyldimethyl chlorosilane) or with an acyl halide to produce a compound in which $R^6$ is acyloxy (e.g. compound 83 made by reaction with acetyl chloride).

The sequence of steps of the processes may be changed. For instance, in Example 2 the steps of brominating to form the 5-bromomethyl compound and then reacting that with a nucleophile are at the end of the process, after the triazolinone ring has been formed. In Example 6 those steps are completed before the amino group on the benzene ring is converted to the triazolinone ring. In Examples 7 and 8 the $R^3$ group is placed on the triazolinone ring as the last step in the process. While in the Examples the X and Y substituents are present in the starting materials, one may instead introduce them at an intermediate or final stage of the process.

The following Examples are given to illustrate the invention further. In this application all proportions are by weight and all temperatures are in °C. unless otherwise indicated.

EXAMPLE 1

Synthesis Of 1-(5-Bromomethyl-4-Chloro-2-Fluorophenyl)-4-Difluoromethyl-4,5-Dihydro-3-Methyl-1,2,4-Triazol-5(H)-One Step A: Synthesis of 2-chloro-4-fluoro-5-nitrotoluene Concentrated sulfuric acid (250 ml) was added to a stirred solution of 2-chloro-4-fluorotoluene (50.0 g, 0.346 mole) in ethylene dichloride (250 ml) at 0° C. Potassium nitrate (35.0 g, 0.346 mole) was then added slowly, maintaining the temperature below 10° C. The reaction was monitored by gas chromatography. Upon the disappearance of 2-chloro-4-fluorotoluene, the reaction mixture was poured into ice and extracted with methylene chloride. The dried organic layer was concentrated under reduced pressure to yield 60.0 g of 2-chloro-4-fluoro-5-nitrotoluene. This reaction was repeated several times.

Step B: Synthesis of 4-chloro-2-fluoro-5-methylaniline

A solution of 2-chloro-4-fluoro-5-nitrotoluene (30.0 g, 0.158 mole) in glacial acetic acid (150 ml) was added to a 250 ml Parr bottle which contained platinum IV oxide (0.4 g). The Parr bottle was placed on a Parr hydrogenation apparatus and charged with hydrogen. The reaction mixture was allowed to shake until hydrogen absorption ceased. The catalyst was removed by vacuum filtration. The filtrate containing 4-chloro-2-fluoro-5-methylaniline was used in the following step. This reaction was repeated several times.

Step C: Synthesis of pyruvic acid, (4-chloro-2-fluoro-5-methylphenyl)hydrazone

A solution of 4-chloro-2-fluoro-5-methylaniline (146 g, 0.770 mole) in acetic acid and concentrated hydrochloric acid (300 ml) was cooled to 0° C., and a solution of sodium nitrite (53.1 g, 0.770 mole) in water (400 ml) was added dropwise, with the tip of the addition funnel below the surface of the solution. The reaction mixture was stirred at 0° C. for 30 minutes and then stannous chloride (260.6 g, 1.155 moles) was added as a ground powder. The precipitated (4-chloro-2-fluoro-5-methylphenyl)hydrazine hydrochloride was dissolved in water and insoluble impurities were removed by filtration. Pyruvic acid (55.6 ml, 0.770 moles) was then added dropwise to the stirred hydrazine hydrochloride intermediate at 0° C. The reaction mixture was allowed to warm to ambient temperature where it stirred for 30 minutes. The yellow product was removed by filtration, dissolved in ethyl acetate, dried and concentrated under reduced pressure to yield 120.0 grams of pyruvic acid, (4-chloro-2-fluoro-5-methyl)phenylhydrazone as a brown solid, m.p. 120° C. dec. The NMR spectrum was consistent with the proposed structure.

Step D: Synthesis of 1-(4-chloro-2-fluoro-5-methylphenyl)-4,5-dihydro-3-methyl-1,2,4-triazol-5(H)-one Triethylamine (49.6 g, 0.490 mole) was added to a stirred solution of pyruvic acid, (4-chloro-2-fluoro-5-methyl)phenylhydrazone (120.0 g, 0.490 mole) in toluene (1.8 L). Upon completion of addition, diphenylphosphoryl azide (135.0 g 0.490 mole) was added dropwise wih stirring. Upon completion of addition, the reaction mixture was heated slowly. Heat was removed when the temperature reached 95° C. The reaction mixture was stirred approximately two hours until nitrogen evolution ceased and the temperature began to decrease, then stirred for an additional one hour. The reaction mixture was poured into ice, the layers were separated and the organic layer was extracted with an aqueous 10% potassium hydroxide solution. The aqueous layers were combined and washed with ether, then acidified with carbon dioxide (dry ice). The white precipitate which formed was removed by filtration. The solid was dissolved in methylene chloride, the water layer was removed and the organic layer was dried and filtered. The filtrate was concentrated under reduced pressure to yield 36.0 g of 1-(4-chloro-2-fluoro-5-methylphenyl)-4,5-dihydro-3-methyl-1,2,4-triazol-5(H)-one, m.p. 179°–181° C. The NMR spectrum was consistent with the proposed structure.

Step E: Synthesis of 1-(4-chloro-2-fluoro-5-methylphenyl)-4-difluoromethyl-4,5-dihydro-3-methyl-1,2,4-triazol-5(H)-one A slurry of 1-(4-chloro-2-fluoro-5-methylphenyl)-4,5-dihydro-3-methyl-1,2,4-triazol-5(H)-one (28.0 g, 0.116 mole) in tetrahydrofuran (200 ml) was added slowly to a stirred mixture of sodium hydride (9.35 g, 0.348 mole) and tetrahydrofuran (300 ml). Upon completion of addition, the reaction mixture was heated at 60° C. When gas evolution ceased, chlorodifluoromethane (26.9 ml, 0.463 mole) was condensed in an addition funnel and added slowly dropwise to the reaction mixture. The chlorodifluoromethane was allowed to recondense continuously for six hours after which time the heating of the reaction mixture was continued with stirring overnight. The reaction mixture was quenched with water, extracted with methylene chloride, dried and concentrated under reduced pressure. The residue was passed through a column of silica gel, eluting with ethyl acetate:hexane (1:19 then 1:4) and finally pure ethyl acetate. Appropriate fractions were combined and concentrated under reduced pressure to yield 7.2 g of 1-(4-chloro-2-fluoro-5-methylphenyl)-4-difluoromethyl-4,5-dihydro-3-methyl-1,2,4-triazol-5(H)-one as a white solid, m.p. 119°–120° C. The NMR spectrum was consistent with the proposed structure. The reaction was repeated several times sometimes using potassium hydroxide and tetrabutylammonium bromide instead of sodium hydride.

Step F: Synthesis of 1-(5-bromomethyl-4-chloro-2-fluorophenyl)-4-difluoromethyl-4,5-dihydro-3-methyl-1,2,4-triazol-5(H)-one A stirred mixture of N-bromosuccinimide (5.25 g, 0.03 mole), 1-(4-chloro-2-fluoro-5-methylphenyl)-4-difluoromethyl-4,5-dihydro-3-methyl-1,2,4-triazol-5(H)-one (8.60 g, 0.30 mole), and benzoyl peroxide (0.5 g) in carbon tetrachloride (200 ml) was heated at reflux overnight. Upon cooling, the reaction mixture was washed with water, dried and concentrated under reduced pressure. The residue was passed through a column of silica gel, eluting with ethyl acetate:hexane (1:9). Appropriate fractions were combined and concentrated under reduced pressure to yield 5.0 g of 1-(5-bromomethyl-4-chloro-2-fluorophenyl)-4-difluoromethyl-4,5-dihydro-3-methyl-1,2,4-triazol-5(H)-one as a white solid. The NMR spectrum was consistent with the proposed structure.

EXAMPLE 2

Synthesis Of 1-[4-Chloro-5-(2Propynylaminomethyl)-2-Fluorophenyl]-4-Difluoromethyl-4,5-Dihydro-3-Methyl-1,2,4-Triazol-5(H)-One A solution of 1-(5-bromomethyl-4-chloro-2-fluorophenyl)-4-difluoromethyl-4,5-dihydro-3-methyl-1,2,4-triazol-5(H)-one (1.5 g, 0.004 mole) in methylene chloride (10 ml) was added dropwise to a stirred solution of propargylamine (1.1 g, 0.02 mole) in methylene chloride (10 ml). Upon completion of addition, the reaction mixture was stirred at ambient temperature for 16 hours. The reaction mixture was diluted with ethyl acetate (200 ml), washed with water (3×50 ml), and dried. The filtrate was concentrated under reduced pressure to yield 1.4 grams of 1-[4-chloro-5-(2-propynylaminomethyl)-2-fluorophenyl]-4-difluoromethyl-4,5-dihydro-3-methyl-1,2,4-triazol-5(H)-one as an oil. The NMR spectrum was consistent with the proposed structure.

EXAMPLE 3

Synthesis Of 1-(4-Chloro-2-Fluoro-5-Methoxyamino-methylphenyl)-4-Difluoromethyl-4,5-Dihydro-3-Methyl-1,2,4-Triazol-5(H)-One This compound was prepared in a manner similar to Example 2 using 1-(5-bromomethyl-4-chloro-2-fluorophenyl)-4-difluoromethyl-4,5-dihydro-3-methyl-1,2,4-triazol-5(H)-one (1.0 g, 0.003 mole), methoxyamine hydrochloride (0.45 g, 0.005 mole), sodium bicarbonate (0.45 g, 0.003 mole), tetrahydrofuran (25 ml) and water (2 ml) to yield 0.02 g of 1-(4-chloro-2-fluoro-5-methoxyaminomethylphenyl)-4-difluoromethyl-4,5-dihydro-3-methyl-1,2,4-triazol-5(H)-one. The NMR spectrum was consistent with the proposed structure.

This reaction was repeated several times sometimes using either sodium hydroxide or sodium bicarbonate in methanol.

EXAMPLE 4

Synthesis Of 1-[5-(N-Acetyl-N-Methoxyaminomethyl)-4-Chloro-2-Fluorophenyl]-4-Difluoromethyl-4,5-Dihydro-3-Ethyl-1,2,4-Triazol-5(H)-One Triethylamine (0.14 g, 0.0014 mole) was added to a stirred solution of 1-(4-chloro-2-fluoro-5-methoxyaminomethylphenyl)-4-difluoromethyl-4,5-dihydro-3-methyl-1,2,4-triazol-5(H)-one (0.5 g, 0.0014 mole) in methylene chloride (5 ml) followed by the addition of acetyl chloride (0.11 g, 0.0014 mole). Upon completion of addition, the reaction mixture was stirred for two hours, then diluted with ether and washed with water (2×5 ml). The dried organic layer was concentrated under reduced pressure to yield 0.54 g of 1-[5-(N-acetyl-N-methoxyaminomethyl)-4-chloro-2-fluorophenyl]-4-difluoromethyl-4,5-dihydro-3-methyl-1,2,4-triazol-5(H)-one as a white solid, m.p. 74°-78° C. The NMR spectrum was consistent with the proposed structure.

EXAMPLE 5

Synthesis Of 1-[4-Chloro-5-[(4-Methyl-4-Methylthio-3-Oxo-3,4,5,6-Tetrahydro-1,2-Oxazin-2-yl)-Methyl]-2-Fluorophenyl]-4-Difluoromethyl-4,5-Dihydro-3-Methyl-1,2,4-Triazol-5(H)-One Step A: Synthesis of alpha-methyl-alpha-methylthiogamma-butyrolactone Under an argon atmosphere, n-butyllithium (1.7 M in hexane, 1800 ml, 3.06 mole) was added slowly to a stirred solution of diisopropylamine (309.4 g, 3.06 mole) in tetrahydrofuran (1800 ml) at −78° C. Upon completion of addition, the reaction mixture was allowed to stir for 30 minutes at which time alpha-methyl-gamma-butyrolactone (278.0 g, 2.78 mole) was added dropwise, also at −78° C. The reaction mixture was stirred 30 minutes then dimethyl disulfide (392.8 g, 4.17 mole) was added dropwise. After stirring for 30 minutes at −78° C., the reaction mixture was warmed to ambient temperature during a one hour period. The reaction mixture was quenched with 5% aqueous hydrochloric acid (1500 ml) and then diluted with ethyl acetate (2000 ml). The layers were separated, and the organic layer was washed with aqueous 10% hydrochloric acid (1×200 ml) and then saturated aqueous sodium bicarbonate (1×100 ml). The organic layer was dried and concentrated under reduced pressure. The residue was distilled to yield 234.6 g of alpha-methyl-alpha-methylthio-gamma-butyrolactone as a colorless oil, b.p. 104°-105° C./8 mm Hg. The NMR spectrum was consistent with the proposed structure.

Step B: Synthesis of ethyl 4-bromo-2-methyl-2-methylthiobutanoate

Hydrogen bromide gas (approximately 1.5 lb) was added to a stirred solution of alpha-methyl-alpha-methylthio-gamma-butyrolactone (234.0 g, 1.59 mole) in ethanol (1000 ml) at 0° C. The reaction mixture was allowed to stir at ambient temperature for 16 hours. Additional hydrogen bromide (1.016) was added, and the reaction mixture was stirred for four days. The reaction mixture was concentrated under reduced pressure until most of the ethanol had been removed, and was then diluted with methylene chloride (400 ml) and washed with water (3×100 l). The dried organic layer was concentrated under reduced pressure. The residue was distilled to yield 280.5 g of ethyl 4-bromo-2-methyl-2-methylthiobutanoate, b.p. 120°-125° C./8 mm Hg. The NMR spectrum was consistent with the proposed structure.

Step C: Synthesis of ethyl 2-methyl-2-methylthio-4-(phthalimidooxy)butanoate

Sodium acetate (53.0 g, 0.647 mole) was added to a stirred solution of N-hydroxyphthalimide (95.9 g, 0.588 mole) in dimethyl sulfoxide (600 ml) under a nitrogen atmosphere. The resulting mixture was stirred for two hours at ambient temperature, then ethyl 4-bromo-2-methyl-2-methylthiobutanoate (150.0 g, 0.588 mole) in dimethyl sulfoxide (400 ml) was added. The reaction mixture was heated at 70°-80° C. for four days. Upon cooling, the reaction mixture was poured into crushed ice and stirred. A solid precipitate was removed by filtration (50 g). The aqueous filtrate was then extracted with ether (500 ml) and methylene chloride (2×250 ml). The extracts were combined, dried and concentrated under reduced pressure to yield a brown oil. The brown oil and the solid precipitate were combined, dissolved in ethyl acetate, and washed with a 1N aqueous solution of sodium hydroxide (3×100 ml) to remove unreacted N-hydroxyphthalimide and dimethyl sulfoxide. The dried organic extract was concentrated under reduced pressure to yield a brown residue. The residue was subjected to column chromatography on silica gel. Elution was accomplished with ethyl acetate:heptane (1:9). Appropriate fractions were combined and concentrated under reduced pressure to yield 93.0 g of ethyl 2-methyl-2-methylthio-4-(phthalimidooxy)butanoate. The NMR spectrum was consistent with the proposed structure.

Step D: Synthesis of ethyl 4-aminooxy-2-methyl-2-methylthiobutanoate hydrochloride Hydrazine hydrate (23.5 g, 0.469 mole) was added to a stirred solution of ethyl 2-methyl-2-methylthio-4-(phthalimidooxy)butanoate (93.0 g, 0.276 mole) in absolute ethanol (800 ml). The reaction mixture was stirred for 16 hours at ambient temperature and then filtered to remove a white precipitate. The filtrate was acidified with concentrated hydrochloride acid and then concentrated under reduced pressure. The residue was dissolved in methylene chloride, and an insoluble solid was removed by filtration. The filtrate was concentrated under reduced pressure, and the residue was dissolved in diethyl ether. Additional insoluble material was removed by filtration, and the filtrate was concentrated under reduced pressure to yield 53.3 g of ethyl 4- aminooxy-2-methyl-2-methylthiobutanoate hydrochloride as a brown oil. The NMR spectrum was consistent with the proposed structure.

Step E: Synthesis of 3,4,5,6-tetrahydro-4-methyl-4-methylthio-2H-1,2-oxazin-3(4H)-one A stirred solution of pyridine (100 ml) and ethyl 4-aminooxy-2-methyl-2-methylthiobutanoate (52.0 g, 0.213 mole) was heated at 70° C. for three days. The reaction mixture was concentrated under reduced pressure to remove most of the pyridine. The residue was dissolved in methylene chloride (200 ml), washed with water (2×50 ml) and dried. The organic layer was concentrated under reduced pressure to yield a light yellow solid which was recrystallized from ethyl acetate:hexane, yielding 11.2 g of 3,4,5,6-tetrahydro-4-methyl-4-methylthio-2H-1,2-oxazin-3(4H)-one as a white solid, m.p. 81°–84° C. The NMR spectrum was consistent with the proposed structure.

Step F: Synthesis of 1-[4-chloro-5-[(4-methyl-4-methylthio-3-oxo-3,4,5,6-tetrahydro-1,2-oxazin-2-yl)methyl]-2-fluorophenyl]-4-difluoromethyl-4,5-dihydro-3-methyl-1,2,4-triazol-5(H)-one A mixture of 3,4,5,6-tetrahydro-4-methyl-4-methylthio-2H-1,2,-oxazin-3(4H)-one (0.44 g, 0.0027 mole), 1-(5-bromomethyl-4-chloro-2-fluorophenyl)-4-difluoromethyl-4,5-dihydro-3-methyl-1,2,4-triazol-5(H)-one (1.00 g, 0.0027), potassium carbonate (0.37 g, 0.0027), and 1,4,7,10,13,16-hexaoxacyclooctadecane (18-crown-6) (0.05 g) in acetonitrile was stirred overnight at ambient temperature. The reaction mixture was diluted with ethyl acetate and washed with water. The dried organic layer was concentrated under reduced pressure to yield 1.21 g of 1-[4-chloro-5-[(4-methyl-4-methylthio-3-oxo-3,4,5,6-tetrahydro-1,2-oxazin-2-yl)methyl]-2-fluorophenyl-4-difluoromethyl-4,5-dihydro-3-methyl-1,2,4-triazol-5(H)-one as a colorless oil. The NMR spectrum was consistent with the proposed structure.

EXAMPLE 6

Synthesis Of
1-[2,4-Dichloro-5-[(4,4-Dimethyl-3-Oxoisoxazolidin-2-yl)Methyl]Phenyl]-4,5-Dihydro-3-Methyl-1,2,4-Triazol-5(H)-One Step A: Synthesis of 2,4-dichloro-5-nitrotoluene To stirred fuming nitric acid (200 ml) at 0° C. was added slowly 2,4-dichlorotoluene (50 g, 0.3mole). Upon completion of addition, the reaction mixture was stirred for one hour, then was poured into water (100 ml). A yellow precipitate was collected by filtration to yield 62.0 g of 2,4-dichloro-5-nitrotoluene, m.p. 40°–44° C.

Step B: Synthesis of (2,4-dichloro-5-nitrophenyl)methyl bromide

This compound was prepared in a manner similar to Example 1 Step F using 2,4-dichloro-5-nitrotoluene (62.0 g, 0.3 mole), N-bromosuccinimide (160.2 g, 0.9 mole), benzoyl peroxide (2.0 g) and carbon tetrachloride (500 ml) to yield (2,4-dichloro-5-nitrophenyl)methyl bromide. The NMR spectrum was consistent with the proposed structure.

Step C: Synthesis of 2-[(2,4-dichloro-5-nitrophenyl)methyl]-4,4-dimethyl-3-isoxazolidinone This compound was prepared in a manner similar to Example 5, Step F using 4,4-dimethyl-3-isoxazolidinone (11.5 g, 0.1 mole), (2,4-dichloro-5-nitrophenyl)methyl bromide, (30 g, 0.1 mole), potassium carbonate (13.8 g, 0.1 mole), 1,4,7,10,13, 16-hexaoxacyclooctadecane (0.5 g, 0.002 mole) and acetonitrile (300 ml). The yield of 2-[(2,4-dichloro-5-nitrophenyl)methyl]-4,4-dimethyl-3-isoxazolidinone was 32.6 g as a yellow solid, m.p 92°–93° C. The NMR spectrum was consistent with the proposed structure.

Step D: Synthesis of 2-[(5-amino-2,4-dichlorophenyl)-methyl]-4,4-dimethyl-3-isoxazolidinone This compound was prepared in a manner similar to Example 1 Step B using 2-[(2,4-dichloro-5-nitrophenyl)-methyl]-4,4-dimethyl-3-isoxazoldinone (31.6 g, 0.1 mole), platinum IV oxide (0.3 g) and morpholine (0.9 g) in methanol (200 ml) instead of acetic acid. The yield of 2-[(5-amino-2,4-dichlorophenyl)methyl]-4,4-dimethyl-3-isoxazolidinone was 17.0 g as a solid. The NMR spectrum was consistent with the proposed structure.

Step E: Synthesis of [2,4-dichloro-5-[(4,4-dimethyl-3-oxoisoxazolidin-2-yl)methyl]phenyl]hydrazine hydrochloride A solution of 2-[(5-amino-2,4-dichlorophenyl)methyl]-4,4-dimethyl-3-isoxazolidinone (16.3 g, 0.564 mole) in concentrated hydrochloric acid (75 ml) was cooled to 0° C., and a solution of sodium nitrite (3.9 g, 0.564 mole) in water (50 ml) was added dropwise with the tip of the addition funnel below the surface of the solution. The reaction mixture temperature was kept below 2° C. during the addition. Upon completion of addition, the reaction mixture was stirred at 0° C. for 30 minutes, and then stannous chloride (28 g, 0.124 mole) in concentrated hydrochloric acid (50 ml) was added dropwise maintaining the temperature below 2° C. The reaction mixture was stirred for one hour at 0° C., and then a tan solid was removed by filtration to yield 10.0 g of [2,4-dichloro-5-[(4,4-dimethyl-3-oxoisoxazolidin-2-yl)methyl]phenyl]hydrazine hydrochloride; m.p. 202°–205° C.

Step F: Synthesis of pyruvic acid, [2,4-dichloro-5-[(4,4-dimethyl-3-oxoisoxazolidin-2-yl)methyl]-phenyl]hydrazone A solution of pyruvic acid (2.6 g, 0.029 mole) in water (50 ml) was added dropwise to a stirred solution of [2,4-dichloro-5-[(4,4-dimethyl-3-oxoisoxazolidin-2-yl)methyl]phenyl]hydrazine hydrochloride (10 g, 0.029 mole) in water (150 ml). Upon completion of addition, the reaction mixture was stirred for one hour. An off-white solid was removed by filtration to yield 6.8 g of pyruvic acid, [2,4-dichloro-5-[(4,4-dimethyl-3-oxoisoxazolidin-2-yl)methyl]phenyl]hydrazone; m.p. 140°–143° C. The NMR spectrum was consistent with the proposed structure.

Step G: Synthesis of 1-[2,4-dichloro-5-[(4,4-dimethyl-3-oxoisoxazolidin-2-yl)methyl]phenyl]-4,5-dihydro-3-methyl-1,2,4-triazol-5(H)-one This compound was prepared in a manner similar to Example 1, Step D using pyruvic acid, [2,4-dichloro-5-[(4,4-dimethyl-3-oxoisoxazolidin-2-yl)methyl]phenyl]-hydrazone (6.2 g, 0.017 mole), triethylamine (1.7 g, 0.017 mole), diphenylphosphoryl azide (4.6 g, 0.017 mole) and toluene (200 ml) to yield 4.2 g of 1-[2,4-dichloro-5-[(4,4-dimethyl-3-oxoisoxazolidin-2-yl)methyl]phenyl]-4,5-dihydro-3-methyl-1,2,4-triazol-5(H)-one. The NMR spectrum was consistent with the proposed structure.

EXAMPLE 7

Synthesis Of
1-[2,4-Dichloro-5-[(4,4-Dimethyl-3-Oxoisoxazolidin-2-yl)Methyl]Phenyl]-4-Ethyl-4,5-Dihydro-3-Methyl-1,2,4-Triazol-5(H)-One This compound was prepared in a manner similar to Example 5 Step F using 1-[2,4-dichloro-5-[(4,4-dimethyl-3-oxoisoxazolidin-2-yl)methyl]phenyl]-4,5-dihydro-3-methyl-1,2,4triazol-5(H)-one (1.0 g, 0.027 mole), bromoethane (0.6 g, 0.0054 mole), potassium carbonate (0.4 g, 0.0027 mole), 1,4,7,10,13,16-hexaoxacyclooctadecane (0.05 g, 0.0002 mole) and acetonitrile to yield 0.65 g of 1-[2,4-dichloro-5-[(4,4-dimethyl-3-oxoisoxazolidin-2-yl)methyl]phenyl]-4-ethyl-4,5-dihydro-3-methyl-1,2,4-triazol-5(H)-one as a yellow oil. The NMR spectrum was consistent with the proposed structure.

EXAMPLE 8

Synthesis Of
1-[4-Chloro-5-[(4,4-Dimethyl-3-Oxoisoxazolidin-2-yl)Methyl]-2-Fluorophenyl]-4-Difluoromethyl-4,5-Dihydro-3-Methyl-1,2,4-Triazol-5(H)-One Potassium hydroxide (0.82 g, 0.0124 mole) and tetrabutylammonium bromide (0.36 g, 0.0011mole) were added to a stirred solution of 1-[4-chloro-5-[(4,4-dimethyl-3-oxoisoxazolidin-2-yl)methyl]-2-fluorophenyl]-4,5-dihydro-3-methyl-1,2,4-triazol-5(H)-one (4.0 g, 0.0113 mole) in tetrahydrofuran (100 ml) and stirred for thirty minutes at ambient temperature. The reaction mixture was cooled in an ice bath, and chlorodifluoromethane (excess) was bubbled through the solution for thirty minutes. The reaction mixture was stirred for one hour at 0° C. and 16 hours at ambient temperature. Ethyl acetate (300 ml) was added to the reaction mixture, which was washed with water (2×50 ml), dried and concentrated under reduced pressure to yield a brown residue. The residue was passed through a column of silica gel, eluting first with ethyl acetate:hexane (1:4) and then pure ethyl acetate. Appropriate fractions were combined and concentrated under reduced pressure to yield 1.5 g of 1-[4-chloro-5-[(4,4-dimethyl-3-oxoisoxazolidin-2-yl)methyl]-2-fluorophenyl]-4-difluoromethyl-4,5-dihydro-3-methyl-1,2,4-triazol-5(H)-one as a solid, m.p. 90°-93° C. The NMR spectrum was consistent with the proposed structure.

EXAMPLE 9

Synthesis Of 1-(4-Chloro-2-Fluoro-5-Phthalimido Methylphenyl)-4-Difluoromethyl-4,5-Dihydro-3-Methyl-1,2,4-Triazol-5(H)-One This compound was prepared in a manner similar to Example 5, Step F using 1-(5-bromomethyl-4-chloro-2-fluorophenyl)-4,5-dihydro-3-methyl-1,2,4-triazol-5(H)-one (10.0 g, 0.027 mole), phthalimide, potassium salt, (5.6 g, 0.03 mole), potassium carbonate (3.7 g, 0.027 mole), and 1,4,7,10,13,16-hexaoxacyclooctadecane (0.5 g) in acetonitrile (100 ml). The yield of 1-(4-chloro-2-fluoro-5-phthalimidomethylphenyl)-4-difluoromethyl-4,5-dihydro-3-methyl-1,2,4-triazol-5(H)-one was 8.9 g; m.p. 152°-154° C. The NMR spectrum was consistent with the proposed structure.

EXAMPLE 10

Synthesis Of
1-(5-Aminomethyl-4-chloro-2-fluorophenyl)-4-Difluoromethyl-4,5-Dihydro-3-Methyl-1,2,4-Triazol-5(H)-One Hydrazine hydrate (2.4 g, 0.04 mole) was added to a stirred solution of 1-(4-chloro-2-fluoro-5-phthalimidomethylphenyl)-4-difluoromethyl-4,5-dihydro-3-methyl-1,2,4-triazol-5(H)-one (8.6 g, 0.02 mole) in methanol (200 ml). The reaction mixture was stirred for 16 hours at ambient temperature, then concentrated under reduced pressure to yield a white solid. The solid was stirred with a solution of 10% aqueous hydrochloric acid (500 ml). The aqueous mixture was filtered, and the filtrate made basic. The alkaline mixture was extracted with methylene chloride (3×50 ml), and the combined extracts were dried and concentrated under reduced pressure to yield 5.1 g of 1-(5-aminomethyl-4-chloro-2-fluorophenyl)-4-difluoromethyl-4,5-dihydro-3-methyl-1,2,4-triazol-5(H)-one, m.p. 88°-90° C. The NMR spectrum was consistent with the proposed structure.

EXAMPLE 11

Synthesis Of
1-[4-Chloro-5-[1-(Ethoxycarbonyl)Ethylaminomethyl]-2-Fluorophenyl]-4-Difluoromethyl-4,5-Dihydro-3-Methyl-1,2,4-Triazol-5(H)-One Borane-tetrahydrofuran complex (1.0M, 3.6 ml, 0.0036 mole) was added slowly by syringe to a stirred mixture of 1-(5-aminomethyl-4-chloro-2-fluorophenyl)-4-difluoromethyl-4,5-dihydro-3-methyl-1,2,4-triazol-5(H)-one (1.0 g, 0.0033 mole), and ethyl pyruvate (0.77 g, 0.0066 mole) in tetrahydrofuran (10 ml) at 0° C. Upon completion of addition the reaction mixture was allowed to warm to ambient temperature and stir for 16 hours. The reaction mixture was poured into aqueous base and ice and then extracted with methylene chloride (3×50 ml). The dried organic extracts were concentrated under reduced pressure. The residue was passed through a column of silica gel eluting with ethyl acetate:heptane (3:7). Appropriate fractions were combined and concentrated under reduced pressure to yield 0.3 g of 1-[4-chloro-5-[1-(ethoxycarbonyl)ethylaminomethyl]-2-fluorophenyl]-4-difluoromethyl-4,5-dihydro-3-methyl-1,2,4-triazol-5(H)-one as an oil. The NMR spectrum was consistent with the proposed structure.

EXAMPLE 12

Synthesis Of
1-(4-Chloro-2-Fluoro-5-Methoxyiminomethylphenyl)-4-Difluoromethyl-4,5-Dihydro-3-Methyl-1,2,4-Triazol-5(H)-One Step A: Synthesis of 1-(5-dibromomethyl-4-chloro-2-fluorophenyl)-4-difluoromethyl-4,5-dihydro-3-methyl-1,2,4-triazol-5(H)-one A stirred stolution of 1-(4-chloro-2-fluoro-5-methylphenyl)-4-difluoromethyl-4,5-dihydro-3-methyl-1,2,4-triazol-5(H)-one (21 g, 0.070 mole), N-bromosuccinimide (26 g, 0.15 mole), benzoyl peroxide (3 g) in 1000 ml of carbon tetrachloride was heated under reflux for three hours. The reaction mixture was cooled and 500 ml of methylene chloride was added. The solution was washed with three 300 ml portions of water. The organic layer was dried with magnesium sulfate and filtered. The filtrate was concentrated under reduced pressure to yield 1-(5-dibromomethyl-4-chloro-2-fluorophenyl)-4-difluoromethyl-4,5-dihydro-3-methyl-1,2,4-triazol-5(H)-one. The NMR spectrum was consistent with the proposed structure.

This reaction was repeated several times.

Step B: Synthesis of 1-(4-chloro-2-fluoro-5-formylphenyl)-4-difluoromethyl-4,5-dihydro-3-methyl-1,2,4-triazol-5(H)-one A stirred solution of 1-(5-dibromomethyl-4-chloro-2-fluoro-phenyl)-4-difluoromethyl-4,5-dihydro-3-methyl-1,2,4-triazol-5(H)-one (42.0 g, 0.093 mole), formic acid (300 ml) and concentrated hydrochloric acid (20 ml) was heated at 90° C. for 18 hours. The reaction mixture was cooled and concentrated under reduced pressure to a residue. The residue was subjected to column chromatography on silica gel. Elution was accomplished using ethyl acetate:heptane (1:4). The appropriate fractions were combined and concentrated under reduced pressure to a residue. The residue was resubjected to column chromatography on silica gel. Elution for the second chromatography was accomplished using ethyl acetate:heptane (1:9). The appropriate fractions were combined and concentrated under reduced pressure to a residue. The residue was recrystallized from ethyl acetate:heptane to yield 1-(4-chloro-2-fluoro-5-formylphenyl)-4-difluoromethyl-4,5-dihydro-3-methyl-1,2,4-triazol-5(H)-one as a solid. The NMR spectrum was consistent with the proposed structure.

Step C: Synthesis of 1-(4-chloro-2-fluoro-5-methoxyiminomethylphenyl)-4-difluoromethyl-4,5-dihydro-3-methyl-1,2,4-triazol-5(H)-one To a stirred solution of methoxylamine hydrochloride (0.3 g, 0.0333 mole) in pyridine (10 ml) was added 1-(4-chloro-2-fluoro-5-formylphenyl)-4-difluoromethyl-4,5-dihydro-3-methyl-1,2,4-triazol-5(H)-one (1.0 g, 0.0033 mole). The reaction mixture was stirred for two hours and then concentrated under reduced pressure to a residue. The residue was stirred in water, and the resultant solid was collected by filtration to yield 1-(4-chloro-2-fluoro-5-methoxyiminomethylphenyl)-4-difluoromethyl-4,5-dihydro-3-methyl-1,2,4-triazol-5(H)-one; m.p. 90°-92° C. The NMR spectrum was consistent with the proposed structure.

EXAMPLE 13

Synthesis Of
1-[4-Chloro-2-Fluoro-5-(2-Fluoroethoxymethyl)-Phenyl]-4-Difluoromethyl-4,5-Dihydro-3-Methyl-1,2,4-Triazol-5(H)-One To a stirred solution of 2-fluoroethanol (0.2 g, 0.003 mole) in tetrahydrofuran (20 ml) was slowly added sodium hydride (0.1 g, 0.003 mole). The reaction mixture was stirred for 15 minutes and 1-(5-bromomethyl-4-chloro-2-fluorophenyl)-4-difluoromethyl-4,5-dihydro-3-methyl-1,2,4-triazol-5(H)-one (1.0 g, 0.0027 mole) was added. The reaction mixture was stirred at ambient temperature for 19 hours and then poured into 200 ml of ethyl acetate. The mixture was washed with three 50 ml portions of water. The organic layer was dried with magnesium sulfate and filtered. The filtrate was concentrated under reduced pressure to a residue. The residue was subjected to column chromatography on silica gel. Elution was accomplished using ethyl acetate:heptane (1:4). The appropriate fractions were combined and concentrated under reduced pressure to yield 1-[4-chloro-2-fluoro-5-(2-fluoroethoxymethyl)phenyl]-4-difluoromethyl-4,5-dihydro-3-methyl-1,2,4-triazol-5(H)-one. The NMR spectrum was consistent with the proposed structure.

EXAMPLE 14

Synthesis Of
1-(4-Chloro-2-Fluoro-5-Methoxymethoxymethylphenyl)-4-Difluoromethyl-4,5-Dihydro-3-Methyl-1,2,4-Triazol-5(H)-One Step A: Synthesis of 1-[4-chloro-2-fluoro-5-(methylcarbonyloxymethyl)phenyl]-4-difluoromethyl-4,5-dihydro-3-methyl-1,2,4-triazol-5(H)-one A solution of 1-(5-bromomethyl-4-chloro-2-fluorophenyl)-4-difluoromethyl-4,5-dihydro-3-methyl-1,2,4-triazol-5(H)-one (5.0 g, 0.014 mole) in dimethylformamide (25 ml) was stirred and sodium acetate (1.2 g, 0.015 mole) was added. The reaction mixture was stirred at ambient temperature for 18 hours and then was diluted with ethyl acetate (275 ml). The mixture was washed with water, dried and filtered. The filtrate was concentrated under reduced pressure to yield 1-[4-chloro-2-fluoro-5-(methylcarbonyloxymethyl)phenyl]-4-difluoromethyl-4,5-dihydro-3-methyl-1,2,4-triazol-5(H)-one (5.2 g) as an oil. The NMR spectrum was consistent with the proposed structure.

Step B: Synthesis of 1-(4-chloro-2-fluoro-5-hydroxymethylphenyl)-4-difluoromethyl-4,5-dihydro-3-methyl-1,2,4-triazol-5(H)-one A mixture of 1-[4-chloro-2-fluoro-5-(methylcarbonyloxymethyl)phenyl]-4-difluoromethyl-4,5-dihydro-3-methyl-1,2,4-triazol-5(H)-one (4.7 g, 0.014 mole) and sodium hydroxide (2.1 g, 0.054 mole) in methanol (50 ml) was stirred at ambient temperature for three hours. The reaction mixture was concentrated under reduced pressure to a residue. The residue was dissolved in methylene chloride and water. The organic layer was separated, washed with water, dried, and filtered. The filtrate was concentrated under reduced pressure to yield 1-(4-chloro-2-fluoro-5-hydroxymethylphenyl)-4-difluoromethyl-4,5-dihydro-3-methyl-1,2,4-triazol-5(H)-one (3.0 g). The NMR spectrum was consistent with the proposed structure.

Step C: Synthesis of 1-(4-chloro-2-fluoro-5-methoxymethoxymethylphenyl)-4-difluoromethyl-4,5-dihydro-3-methyl-1,2,4-triazol-5(H)-one A solution of 1-(4-chloro-2-fluoro-5-hydroxymethylphenyl)-4-difluoromethyl-4,5-dihydro-3-methyl-1,2,4-triazol-5(H)-one (1.0 g, 0.003 mole) in methylene chloride (20 ml) was stirred, and sodium hydride (0.1 gram, 0.003 mole) was slowly added. The reaction mixture was stirred for 15 minutes and bromomethyl methyl ether (0.6 g, 0.005 mole) was added. The reaction mixture was stirred at ambient temperature for 3.5 hours and then poured into ethyl acetate. The mixture was washed with three 50 ml portions of water. The organic layer was dried with magnesium sulfate and filtered. The filtrate was concentrated under reduced pressure to a residue. The residue was subjected to column chromatography on silica gel. Elution was accomplished using ethyl acetate:heptane (1:4). The appropriate fractions were combined and concentrated under reduced pressure to yield 1-(4-chloro-2-fluoro-5-methoxymethoxymethylphenyl)-4-difluoromethyl-4,5-dihydro-3-methyl-1,2,4-triazol-5(H)-one. The NMR spectrum was consistent with the proposed structure.

EXAMPLE 15

Synthesis Of
1-(4-Chloro-5-Ethylthiomethyl-2-Fluorophenyl)-4-Difluoromethyl-4,5-Dihydro-3-Methyl-1,2,4-Triazol-5(H)-One A solution of 1-(5-bromomethyl-4-chloro-2-fluorophenyl)-4-difluoromethyl-4,5-dihydro-3-methyl-1,2,4-triazol-5(H)-one (5.0 g, 0.008 mole) in dimethylformamide (20 ml) was stirred, and the sodium salt of ethyl mercaptan (1.0 g, 0.012 mole) was slowly added. The reaction mixture was stirred at ambient temperature for five hours and then poured into ethyl acetate (200 ml). The mixture was washed with water, dried with magnesium sulfate, and filtered. The filtrate was concentrated under reduced pressure to yield 1-(4-chloro-5-ethylthiomethyl-2-fluorophenyl)-4-difluoro-4,5-dihydro-3-methyl-1,2,4-triazol-5(H)-one (3.0 g). The NMR spectrum was consistent with the proposed structure.

EXAMPLE 16

Synthesis Of 1-(4-Chloro-5-Ethylsulfinylmethyl-b 2-Fluorophenyl)-4-Difluoromethyl-4,5-Dihydro-3-Methyl-1,2,4-Triazol-5(H)-One A solution of 1-(4-chloro-5-ethylthiomethyl-2-fluorophenyl)-4-difluoromethyl-4,5-dihydro-3-methyl-1,2,4-triazol-5(H)-one (1.4 g, 0.004 mole) in methylene chloride (50 ml) was stirred, and 85% m-chloroperoxybenzoic acid (0.8 g, 0.004 mole) was added. The reaction mixture was stirred at ambient temperature for 16 hours and then poured into ethyl acetate (200 ml). The mixture was washed with three 50 ml portions of aqueous sodium bicarbonate solution, dried with magnesium sulfate, and filtered. The filtrate was concentrated under reduced pressure to a residue. The residue was subjected to column chromatography on silica gel. Elution was accomplished using ethyl acetate. The appropriate fractions were combined and concentrated under reduced pressure to yield 1-(4-chloro-5-ethylsulfinylmethyl-2-fluorophenyl)-4-difluoromethyl-4,5-dihydro-3-methyl-1,2,4-triazol-5(H)-one; m.p. 104°–108° C. The NMR spectrum was consistent with the proposed structure.

EXAMPLE 17

Synthesis Of
4-Chloro-2-Fluoro-5-(1-Methoxyethyl)Aniline

Step A: Synthesis of 2-chloro-4-fluorobenzal bromide

In a flask were placed 150 g (1.04 moles) of 2-chloro-4-fluorotoluene, 391 g (2.20 moles) of N-bromosuccinimide, 3 g (0.012 mole) of benzoyl peroxide, and 800 ml of carbon tetrachloride. This mixture was refluxed overnight and then filtered. The solvent was evaporated under reduced pressure, leaving a residue of impure 2-chloro-4-fluorobenzal bromide weighing 340 g.

Step: Synthesis of 2-chloro-4-fluorobenzaldehyde

In a flask were placed 30.25 g (0.100 mole) of 2-chloro-4-fluorobenzal bromide, 45 ml (1.2 mole) of formic acid, and 15 ml of concentrated hydrochloric acid. This mixture was heated at 100°–105° C. overnight. After cooling to room temperature, the reaction mixture was poured into 200 ml of an ice/water mixture which was then extracted twice with diethyl ether. The combined extracts were washed successively with a saturated, aqueous, sodium bicarbonate solution and water. After being dried over anhydrous magnesium sulfate, the extract was filtered, and the solvent was evaporated under reduced pressure, leaving 17 g of 2-chloro-4-fluorobenzaldehyde as a residue.

Step C: Synthesis of 1-(2-chloro-4-fluorophenyl)-ethanol

A solution of 5.25 g (0.033 mole) of 2-chloro-4-fluorobenzaldehyde in 100 ml of diethyl ether was cooled to −10° C., and 11.2 ml (0.033 mole) of a 2.95 M solution of methylmagnesium bromide in diethyl ether was added dropwise with stirring. The reaction mixture was warmed to 0° C. and was stirred for several hours. After warming to room temperature, the reaction mixture was poured into an ice/water mixture. The resulting mixture was extracted with methylene chloride. The solvent was evaporated from the extract under reduced pressure, and the residue was passed through a column of silica gel, eluting first with heptane and then with ethyl acetate/heptane (1/9). The appropriate fractions were combined, and the solvent was evaporated under reduced pressure, leaving 1.46 g of 1-(2-chloro-4-fluorophenyl)ethanol as an amber oil. The nmr and ir spectra were consistent with the proposed structure. This reaction was repeated on a larger scale to provide sufficient 1-(2-chloro-4-fluorophenyl)ethanol for Step D.

Step D: Synthesis of 1-(2-chloro-4-fluoro-5-nitrophenyl)ethyl nitrate

A solution of 176 ml of fuming nitric acid in 25 ml of 1,2-dichloroethane was cooled to −20° C. To this solution was added dropwise a solution of 20 g (0.115 mole) of 1-(2-chloro-4-fluorophenyl)ethanol in 25 ml of 1,2-dichloroethane. During the addition which required 45 minutes, the reaction mixture temperature was maintained between −24° C. and −20° C. Stirring was continued at this temperature for 15 minutes following completion of addition, and then 150 ml of methylene chloride was added to he reaction mixture. After warming slowly to 0° C., the reaction mixture was slowly poured into an ice/water mixture. The organic phase was separated from the aqueous phase, and the latter was extracted four times with 50 ml of methylene chloride. The organic phase and the extracts were combined and were washed successively twice with cold water and three times with a cold, aqueous solution of sodium bicarbonate. The organic phase was dried over anhydrous magnesium sulfate, filtered, and the solvent was evaporated under reduced pressure, yielding 26 g of 1-(2-chloro-4-fluoro-5-nitrophenyl)ethyl nitrate as a residue. The nmr and ir spectra were consistent with the proposed structure.

Step E: Synthesis of 1-(2-chloro-4-fluoro-5-methylcarbonylaminophenyl)ethyl nitrate In a Parr hydrogenation apparatus were placed 3.7 g (0.014 mole) of 1-(2-chloro-4-fluoro-5-nitrophenyl)ethyl nitrate, 0.35 g of platinum oxide catalyst, 35 ml of ethyl acetate, and 10 ml of acetic anhydride. The apparatus was pressurized with hydrogen, and the reaction was allowed to continue until the pressure ceased dropping. The reaction mixture was filtered, and the filtrate was concentrated under reduced pressure leaving a residue. This residue was mixed with 15 ml of water and 5 ml of 10% hydrochloric acid. This mixture was stirred at room temperature for two hours. Following dilution with water, the mixture was extracted with methylene chloride. The extracts were combined and washed successively with water, 5% hydrochloric acid, and a saturated, aqueous solution of sodium bicarbonate. This solution was dried, filtered, and the solvent was evaporated under reduced pressure leaving a residue. This residue was passed through a column of silica gel, eluting first with ethyl acetate/heptane (¼) and then with ethyl acetate/heptane (1/1). The appropriate fractions were collected, and the solvent was evaporated under reduced pressure yielding 1.7 g of 1-(2-chloro-4-fluoro-5-methylcarbonylaminophenyl)ethyl nitrate as a white solid. The nmr and ir spectra were consistent with the proposed structure.

Step F: Synthesis of N-[4-chloro-2-fluoro-5-(1-methoxyethyl)phenyl]acetamide

To a clear, colorless solution of 0.4 g (0.0015 mole) of 1-(2-chloro-4-fluoro-5-methylcarbonylaminophenyl)ethyl nitrate in 15 ml of absolute methanol was added dropwise 0.31 g (0.0015 mole) of a 25 weight percent solution of sodium methoxide in methanol. The reaction mixture turned pale yellow immediately and was stirred at room temperature for 2.5 hours. An additional 0.31 g (0.0015 mole) of the sodium methoxide solution was added, and stirring at room temperature continued for 18 hours. The mixture was heated at reflux for 2.5 hours and then was allowed to cool to room temperature. To the mixture was added 100 ml of diethyl ether, and this mixture was washed with water. The diethyl ether solution was dried, filtered, and the solvent was evaporated under reduced pressure, yielding 0.28 g of N-[4-chloro-2-fluoro-5-(1-methoxyethyl)-phenyl]acetamide. The nmr and ir spectra were consistent with the proposed structure. This reaction was repeated to provide sufficient starting material for Step G.

Step G: Synthesis of 4-chloro-2-fluoro-5-(1-methoxyethyl)aniline

A mixture of 0.6 g (0.0024 mole) of N-[4-chloro-2-fluoro-5-(1-methoxyethyl)phenyl]acetamide, 0.14 g (0.0025 mole) of potassium hydroxide, 10 ml of water, and 10 ml of methanol was heated at reflux for 24 hours. This mixture was cooled and diluted with 50 ml of water. The resulting mixture was extracted successively with methylene chloride and diethyl ether. The combined extracts were dried, filtered, and the solvent was evaporated under reduced pressure, leaving 0.58 g of 4-chloro-2-fluoro-5-(1-methoxyethyl)aniline as an oil. The nmr spectrum was consistent with the proposed structure.

HERBICIDAL ACTIVITY

The plant test species used in demonstrating the herbicidal activity of compounds of this invention include cotton (*Gossypium hirsutum* var. Stoneville), soybean (*Glycine max* var. Williams), field corn (*Zea mays* var. Agway 595S), wheat (*Triticum aestivium* var. Prodax), rice (*Oryza sativa*), field bindweed (*Convolvulus arvensis*), morningglory (*Ipomea lacumosa* or *Ipomea hederacea*), velvetleaf (*Abutilon theophrasti*), barnyardgrass (*Echinochloa crus galli*), green foxtail (*Setaria viridis*), johnsongrass (*Sorghum halepense*), and yellow nutsedge (*Cyperus esculentus*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered, then drenched with the appropriate amount of a solution of the test compound in a 50/50 mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiples thereof. The flats were placed in a greenhouse and watered regularly at the soil surface for 21 days at which time phytotoxicity data were recorded.

The flats for the postemergence test were placed in a greenhouse and watered for 8-10 days, then the foliage of the emerged test plants was sprayed with a solution of the test compound in acetone-water containing up to 0.5% sorbitan monolaurate. After spraying, the foliage was kept dry for 24 hours, then watered regularly for 21 days, and phytotoxicity data recorded.

Phytotoxicity data were taken either as percent kill or percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The present rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery | Deficient to moderate weed control |
| 60 | | Lasting crop injury no recovery | Moderate weed control |
| 70 | Severe | Heavy injury and stand loss | Control somewhat less than satisfactory |
| 80 | | Crop nearly destroyed a few survivors | Satisfactory to good weed control |
| 90 | | Only occasional live plants left | Very good to excellent control |
| 100 | Complete effect | Complete crop destruction | Complete weed destruction |

Herbicidal data at selected application rates are given for various compounds of the invention in Tables 3 and 4 below. The test compounds are identified by numbers which correspond to those used in Table 1.

In the Table of herbicidal data below, "kg/ha" is kilograms per hectare, "% K" is percent kill, and "% C" is percent control.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules (e.g. for paddy rice) in the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 0.8 parts of the herbicidal compound 17.9 parts of Palmetto clay, and 1.0 part of sodium lignosulfonate and 0.3 part of sulfonated aliphatic polyester as wetting agents. Other wettable podwer formulations are:

| Component: | % by Wt. |
|---|---|
| Active ingredient | 40.00 |
| Sodium ligninsulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium ligninsulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate. | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acids esters of polyhydric alcohols and the ethylene oxide addition products of such esters; and the addition product of long-chain mercaptans and ethylene oxide. Many other types of useful surface-active agents are avaiable in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

|  | % by Wt. |
|---|---|
| Oil Suspension: | |
| Active ingredient | 25.00 |
| polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. Weed control is achieved at low concentrations of the herbicides of this invention; for instance, compound 52 of the tables below has, in greenhouse testing at pre-emergence dosages as low as about 0.03 and 0.06 kg/ha, given good weed control with no damage to cotton. For field use, where there are losses of herbicide, larger dosages (e.g. four to ten times the dosage mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)-glycine (diethatyl-ethyl); benzothiadiazinone herbicides such as 3-(1-methylethyl)-(1H) 2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6(ethylamino)-1,3,5-triazin-2-yl]amino-2-methyl-propanenitrile (cyanazine); dinitrolaniline herbicides such as 2,6-dinitro-N,N-dipropyl-4-(trifluoromethyl)-benzeneamine (trifluralin); and aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

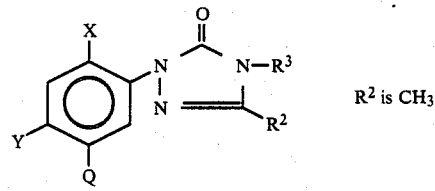

$R^2$ is $CH_3$

| Cmpd. No. | X | Y | Q | $R^3$ |
|---|---|---|---|---|
| 1 | F | Cl | $CH_2NH_2$ | $CHF_2$ |
| 2 | F | Cl | $CH_2NHCH_2C\equiv CH$ | $CHF_2$ |
| 3 | F | Cl | $CH_2NHCH(CH_3)CO_2C_2H_5$ | $CHF_2$ |
| 4 | F | Cl | $CH_2NHOCH_3$ | $CHF_2$ |
| 5 | F | Cl | $CH_2NHC(O)CH_3$ | $CHF_2$ |
| 6 | F | Cl | $CH_2NHC(O)OC_2H_5$ | $CHF_2$ |
| 7 | F | Cl | $CH_2NHC(O)NHCH_3$ | $CHF_2$ |
| 8 | F | Cl | $CH_2NHSO_2CH_3$ | $CHF_2$ |
| 9 | F | Cl | $CH_2N(C_2H_5)_2$ | $CHF_2$ |
| 10 | F | Cl | $CH_2N\underset{\underline{\hspace{2cm}}}{-CH_2CH_2OCH_2CH}$ | $CHF_2$ |

TABLE 1-continued

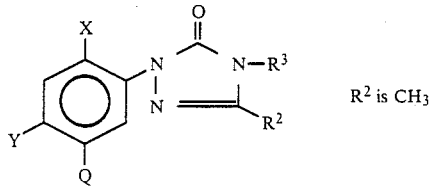

R² is CH₃

| Cmpd. No. | X | Y | Q | R³ |
|---|---|---|---|---|
| 11 | F | Cl | CH₂N(OCH₃)C(O)CH₃ | CHF₂ |
| 12 | F | Cl | CH₂N(OCH₃)C(O)CH₂F | CHF₂ |
| 13 | F | Cl | CH₂N(OCH₃)C(O)CH₂Cl | CHF₂ |
| 14 | F | Cl | CH₂N(OCH₃)C(O)CHF₂ | CHF₂ |
| 15 | F | Cl | CH₂N(OCH₃)C(O)CF₃ | CHF₂ |
| 16 | F | Cl | CH₂N(OCH₃)C(O)C(CH₃)₃ | CHF₂ |
| 17 | F | Cl | CH₂N(OCH₃)C(O)C(CH₃)₂CH₂Cl | CHF₂ |
| 18 | F | Cl | CH₂N(OCH₃)C(O)CH=CH₂ | CHF₂ |
| 19 | F | Cl | CH₂N—C(O)C(CH₃)₂CH₂O | H |
| 20 | F | Cl | CH₂N—C(O)C(CH₃)₂CH₂O | CHF₂ |
| 21 | Cl | Cl | CH₂N—C(O)C(CH₃)₂CH₂O | H |
| 22 | Cl | Cl | CH₂N—C(O)C(CH₃)₂CH₂O | CHF₂ |
| 23 | Cl | F | CH₂N—C(O)C(CH₃)₂CH₂O | H |
| 24 | Cl | Cl | CH₂N—C(O)C(CH₃)₂CH₂O | C₂H₅ |
| 25 | Cl | Cl | CH₂N—C(O)C(CH₃)₂CH₂O | C₃H₇(n) |
| 26 | F | Cl | CH₂N—C(O)C(CH₃)₂CH₂O | CH₂CH=CH₂ |
| 27 | Cl | Cl | CH₂N—C(O)C(CH₃)₂CH₂O | CH₂CH=CH₂ |
| 28 | Cl | Cl | CH₂N—C(O)C(CH₃)₂CH₂O | CH₂C≡CH |
| 29 | Cl | Cl | CH₂N—C(O)C(CH₃)₂CH₂O | CH₂CN |
| 30 | Cl | Cl | CH₂N—C(O)C(CH₃)₂CH₂O | CH₂CO₂C₂H₅ |
| 31 | Cl | Cl | CH₂N—C(O)C(CH₃)₂CH₂O | CH₂C₆H₅ |
| 32 | Cl | Cl | CH₂N—C(O)C(CH₃)₂CH₂O | CH₂C₆H₄(2-Cl) |
| 33 | F | Cl | CH₂N—C(O)C(CH₃)(SCH₃)CH₂CH₂O | CHF₂ |
| 34 | F | Cl | CH₂N(OCH₃)SO₂CH₃ | CHF₂ |
| 35 | F | Cl | CH₂N(OCH₃)SO₂CF₃ | CHF |
| 36 | F | Cl | CH₂N(OCH₃)S(O)₂C₆H₄(2-Cl) | CHF₂ |
| 37 | F | Cl | CH₂N(OCH₃)S(O₂)C₆H₄(4-OCH₃) | CHF₂ |
| 38 | F | Cl | CH₂N(OCH₃)S(O₂)C₆H₄(2-CO₂CH₃) | CHF₂ |

TABLE 1-continued

[Structure: phenyl ring with X, Y, Q substituents attached to N=N-C(=O)-N(R³) ring with =CR² ; R² is CH₃]

| Cmpd. No. | X | Y | Q | R³ |
|---|---|---|---|---|
| 39 | Cl | F | CH—NHC(O)C(CH₃)₂CH₂O (ring) | H |
| 40 | Cl | F | CH—NHC(O)C(CH₃)₂CH₂O (ring) | CHF₂ |
| 41 | Cl | Cl | CHN(CH₃)C(O)C(CH₃)₂CH₂O (ring) | CH₃ |
| 42 | Cl | Cl | CH—NHC(O)C(CH₃)₂CH₂O (ring) | CHF₂ |
| 43 | Cl | Cl | CH—N(CH₂CH=CH₂)C(O)C(CH₃)₂CH₂O (ring) | CH₂CH=CH₂ |
| 44 | F | Br | CH—NHC(O)C(CH₃)₂CH₂O (ring) | CHF₂ |
| 45 | F | Cl | CH₂N(C(O))₂C₆H₄ (phthalimide) | CHF₂ |
| 46 | F | Cl | CH₂NH—A* | CHF₂ |
| 47 | F | Cl | CH₂N[C(O)CH₃]A* | CHF₂ |
| 48 | F | Cl | CH₂N(SO₂CH₃)A* | CHF₂ |
| 49 | F | Cl | CH₂N(A*)₂ | CHF₂ |
| 50 | F | Cl | CH₂OH | CHF₂ |
| 51 | F | Cl | CH₂OCH₃ | CHF₂ |
| 52 | F | Cl | CH₂OC₂H₅ | CHF₂ |
| 53 | F | Cl | CH₂OCH₂CH₂F | CHF₂ |
| 54 | F | Cl | CH₂OCH(CH₃)₂ | CHF₂ |
| 55 | F | Cl | CH₂OCH(CH₂F)₂ | CHF₂ |
| 56 | F | Cl | CH₂OCH₂cyclopropyl | CHF₂ |
| 57 | F | Cl | CH₂OCH₂CH=CH₂ | CHF₂ |
| 58 | F | Cl | CH₂OCH₂C≡CH | CHF₂ |
| 59 | Cl | Cl | CH₂OCH₂C≡CH | CHF₂ |
| 60 | F | Cl | CH₂OCH₂OCH₃ | CHF₂ |
| 61 | F | Cl | CH₂OC₂H₄OCH₃ | CHF₂ |
| 62 | F | Cl | CH₂O—tetrahydropyran-2-yl | CHF₂ |
| 63 | F | Cl | CH₂O—tetrahydrofuran-3-yl | CHF₂ |
| 64 | F | Cl | CH₂OC(O)CH₃ | CHF₂ |
| 65 | F | Cl | CH₂OC(O)CH₂F | CHF₂ |
| 66 | F | Cl | CH₂OC(O)CH₂CH₂Cl | CHF₂ |
| 67 | F | Cl | CH₂OCH₂CO₂C₂H₅ | CHF₂ |
| 68 | F | Cl | CH₂ONO₂ | CHF₂ |
| 69 | F | Cl | CH₂OC₆H₅ | CHF₂ |
| 70 | F | Cl | CH₂OC₆H₃(2-Cl,4-CF₃) | CHF₂ |
| 71 | F | Cl | CH₂OCH₂C₆H₅ | CHF₂ |
| 72 | F | Cl | CH₂SCH₃ | CHF₂ |
| 73 | F | Cl | CH₂SC₂H₅ | CHF₂ |
| 74 | F | Cl | CH₂SCH₂CH=CH₂ | CHF₂ |
| 75 | F | Cl | CH₂SCH₂CO₂CH₃ | CHF₂ |
| 76 | F | Cl | CH₂SCN | CHF₂ |
| 77 | F | Cl | CH₂S(O)C₂H₅ | CHF₂ |
| 78 | F | Cl | CH₂S(O)CH₂CH=CH₂ | CHF₂ |
| 79 | F | Cl | CH₂S(O)₂C₂H₅ | CHF₂ |
| 80 | F | Cl | CH₂S(O)₂CH₂CH=CH₂ | CHF₂ |
| 81 | F | Cl | CH=NOH | CHF₂ |
| 82 | F | Cl | CH=NOCH₃ | CHF₂ |
| 83 | F | Cl | CH=NOC(O)CH₃ | CHF₂ |
| 84 | F | Cl | CH=NOSi(CH₃)₂C(CH₃)₃ | CHF₂ |
| 85 | F | Cl | CH=NOC₂H₅ | CHF₂ |
| 86 | F | Cl | CH=NOCH(CH₃)₂ | CHF₂ |
| 87 | F | Cl | CH=NOCH₂CH(CH₃)₂ | CHF₂ |
| 88 | F | Cl | CH=NOCH₂CH=CH₂ | CHF₂ |
| 89 | F | Cl | CH=NOCH₂C≡CH | CHF₂ |

TABLE 1-continued

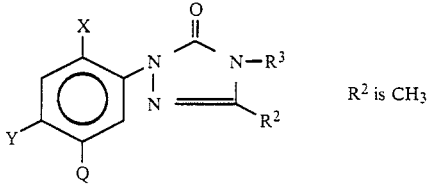

R² is CH₃

| Cmpd. No. | X | Y | Q | R³ |
|---|---|---|---|---|
| 90 | F | Cl | C(CH₃)=NOH | CHF₂ |
| 91 | F | Cl | C(CH₃)=NOCH₃ | CHF₂ |
| 92 | F | Cl | C(CH₃)=NOC₂H₅ | CHF₂ |
| 93 | F | Cl | C(CH₃)=NOCH(CH₃)₂ | CHF₂ |
| 94 | F | Cl | C(CH₃)=NOCH₂CH(CH₃)₂ | CHF₂ |
| 95 | F | Cl | C(CH₃)=NOCH₂CH=CH₂ | CHF₂ |
| 96 | F | Cl | C(CH₃)=NOCH₂C≡CH | CHF₂ |
| 97 | F | Cl | CH₂OC₂H₅ | CF₂CHF₂ |
| 98 | F | Cl | CH₂OC₂H₅ | CF₂CHClF |
| 99 | F | Cl | CH₂OC₂H₅ | CH₂CF₃ |
| 100 | F | Cl | CH₂NHCH₂C≡C—CH₃ | CHF₂ |
| 101 | F | Cl | CH₂NHCH(CH₃)CO₂H | CHF₂ |
| 102 | F | Cl | CH₂NHCH(CH₃)CO₂CH₃ | CHF₂ |
| 103 | F | Cl | CH₂NHCH(CH₃)CO₂C₃H₇(n) | CHF₂ |
| 104 | F | Cl | CH₂NHCH(CH₃)CO₂CH(CH₃)₂ | CHF₂ |
| 105 | F | Cl | CH₂NHCH(CH₃)CO₂C₄H₉(n) | CHF₂ |
| 106 | F | Cl | CH₂NHCH(CH₃)CO₂C₅H₁₁(n) | CHF₂ |
| 107 | F | Cl | CH₂NHOC₂H₅ | CHF₂ |
| 108 | F | Cl | CH₂NHOC₃H₇(n) | CHF₂ |
| 109 | F | Cl | CH₂NHOCH₂C₆H₅ | CHF₂ |
| 110 | F | Cl | CH₂NHCO₂CH₃ | CHF₂ |
| 111 | F | Cl | CH₂NHCO₂C(CH₃)₃ | CHF₂ |
| 112 | F | Cl | CH₂NHC(O)C₂H₅ | CHF₂ |
| 113 | F | Cl | CH₂NHC(O)C₃H₇(n) | CHF₂ |
| 114 | F | Cl | CH₂NHC(O)CH₂Cl | CHF₂ |
| 115 | F | Cl | CH₂NHC(O)CHCl₂ | CHF₂ |
| 116 | F | Cl | CH₂NHC(O)CCl₃ | CHF₂ |
| 117 | F | Cl | CH₂NHC(O)CH₂F | CHF₂ |
| 118 | F | Cl | CH₂NHC(O)CHF₂ | CHF₂ |
| 119 | F | Cl | CH₂NHC(O)C(CH₃)₂CH₂Cl | CHF₂ |
| 120 | F | Cl | CH₂NHC(O)C(CH₃)₂CH₂Br | CHF₂ |
| 121 | F | Cl | CH₂NHC(O)C₆H₅ | CHF₂ |
| 122 | F | Cl | CH₂NHC(O)C₆H₄(2-Cl) | CHF₂ |
| 123 | F | Cl | CH₂NHC(O)C₆H₄(4-Cl) | CHF₂ |
| 124 | F | Cl | CH₂NHC(O)C₆H₄(4-CH₃) | CHF₂ |
| 125 | F | Cl | CH₂NHC(O)C₆H₄(4-OCH₃) | CHF₂ |
| 126 | F | Cl | CH₂NHC(O)C₆H₄(4-NO₂) | CHF₂ |
| 127 | F | Cl | CH₂NHC(O)C₆H₄(4-OCF₃) | CHF₂ |
| 128 | F | Cl | CH₂NHC(O)C₆H₄(4-CN) | CHF₂ |
| 129 | F | Cl | CH₂NHC(O)CH₂C₆H₅ | CHF₂ |
| 130 | F | Cl | CH₂NHC(O)CH₂OC₆H₅ | CHF₂ |
| 131 | F | Cl | CH₂NHC(O)CH₂OC₆H₃(2,4-Cl₂) | CHF₂ |
| 132 | F | Cl | CH₂NHC(O)NHC₆H₅ | CHF₂ |
| 133 | F | Cl | CH₂NHC(O)NHC₆H₃(3,4-Cl₂) | CHF₂ |
| 134 | F | Cl | CH₂NHC(O)N(CH₃)₂ | CHF₂ |
| 135 | F | Cl | CH₂NHC(O)NHC₂H₅ | CHF₂ |
| 136 | F | Cl | CH₂NHSO₂C₂H₅ | CHF₂ |
| 137 | F | Cl | CH₂NHSO₂CF₃ | CHF₂ |
| 138 | F | Cl | CH₂NHSO₂C₃H₇(n) | CHF₂ |
| 139 | F | Cl | CH₂NHSO₂C₆H₅ | CHF₂ |
| 140 | F | Cl | CH₂N(CH₃)₂ | CHF₂ |
| 141 | F | Cl | CH₂NCH₂(CH₂)₃CH₂ | CHF₂ |
| 142 | F | Cl | CH₂NCH₂(CH₂)₂CH₂ | CHF₂ |
| 143 | F | Cl | CH₂N[CH(CH₃)₂]₂ | CHF₂ |
| 144 | F | Cl | CH₂N(OCH₂C₆H₅)C(O)CH₃ | CHF₂ |
| 145 | F | Cl | CH₂N(OCH₂C₆H₅)C(O)CH₂F | CHF₂ |
| 146 | F | Cl | CH₂N(OC₂H₅)C(O)CH₃ | CHF₂ |
| 147 | F | Cl | CH₂N(CH₃)C(O)CH₃ | CHF₂ |
| 148 | F | Cl | CH₂N(C₂H₅)C(O)CH₃ | CHF₂ |
| 149 | F | Cl | CH₂N(OCH₃)C(O)C(CH₃)=CH₂ | CHF₂ |
| 150 | F | Cl | CH₂N(OCH₃)C(O)C(CH₃)=CHCH₃ | CHF₂ |
| 151 | F | Cl | CH₂N(OCH₃)C(O)CH=CHCH₃ | CHF₂ |

TABLE 1-continued

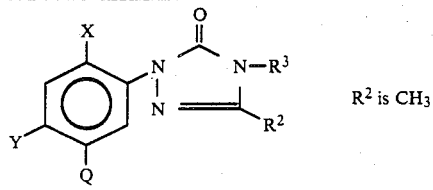

R² is CH₃

| Cmpd. No. | X | Y | Q | R³ |
|---|---|---|---|---|
| 152 | F | Cl | CH₂NC(O)CH(CH₃)CH₂O | CHF₂ |
| 153 | F | Cl | CH₂NC(O)CH₂CH₂O | CHF₂ |
| 154 | F | Br | CH₂NC(O)C(CH₃)₂CH₂O | CHF₂ |
| 155 | F | F | CH₂NC(O)C(CH₃)₂CH₂O | CHF₂ |
| 156 | Cl | CF₃ | CH₂NC(O)C(CH₃)₂CH₂O | CHF₂ |
| 157 | F | CF₃ | CH₂NC(O)C(CH₃)₂CH₂O | CHF₂ |
| 158 | Cl | NO₂ | CH₂NC(O)C(CH₃)₂CH₂O | CHF₂ |
| 159 | F | NO₂ | CH₂NC(O)C(CH₃)₂CH₂O | CHF₂ |
| 160 | Br | Cl | CH₂NC(O)C(CH₃)₂CH₂O | CHF₂ |
| 161 | F | Br | CH₂N(OCH₃)C(O)CH₃ | CHF₂ |
| 162 | F | F | CH₂N(OCH₃)C(O)CH₃ | CHF₂ |
| 163 | F | CF₃ | CH₂N(OCH₃)C(O)CH₃ | CHF₂ |
| 164 | Cl | CF₃ | CH₂N(OCH₃)C(O)CH₃ | CHF₂ |
| 165 | F | NO₂ | CH₂N(OCH₃)C(O)CH₃ | CHF₂ |
| 166 | Cl | NO₂ | CH₂N(OCH₃)C(O)CH₃ | CHF₂ |
| 167 | Br | Cl | CH₂N(OCH₃)C(O)CH₃ | CHF₂ |
| 168 | Cl | F | CH₂N(OCH₃)C(O)CH₃ | CHF₂ |
| 169 | Cl | Br | CH₂N(OCH₃)C(O)CH₃ | CHF₂ |
| 170 | Cl | F | CH₂OCH₃ | CHF₂ |
| 171 | Cl | F | CH₂OC₂H₅ | CHF₂ |
| 172 | Cl | F | CH₂OCH(CH₃)₂ | CHF₂ |
| 173 | Cl | F | CH₂OCH₂CH=CH₂ | CHF₂ |
| 174 | Cl | F | CH₂OCH₂C≡CH | CHF₂ |
| 175 | F | Br | CH₂OCH₃ | CHF₂ |
| 176 | F | Br | CH₂OC₂H₅ | CHF₂ |
| 177 | F | NO₂ | CH₂OC₂H₅ | CHF₂ |
| 178 | F | CF₃ | CH₂OC₂H₅ | CHF₂ |
| 179 | F | Cl | CH₂OCH₂CO₂CH₃ | CHF₂ |
| 180 | F | Cl | CH₂OCH₂CO₂H | CHF₂ |
| 181 | F | Cl | CH₂OCH₂CO₂CH(CH₃)₂ | CHF₂ |
| 182 | Cl | F | CH₂SCH₃ | CHF₂ |
| 183 | Cl | Br | CH₂SC₂H₅ | CHF₂ |
| 184 | F | Cl | CH₂SCH₂C≡CH | CHF₂ |
| 185 | F | Cl | CH₂SCH₂CH=CH₂ | CHF₂ |
| 186 | F | Cl | CH=NOCH₂C₆H₅ | CHF₂ |
| 187 | F | Cl | CH=NOC₃H₇(n) | CHF₂ |
| 188 | F | Cl | C(CH₃)=NOC(O)CH₃ | CHF₂ |
| 189 | F | Cl | CH(CH₃)OCH₃ | CHF₂ |
| 190 | F | Cl | CH(CH₃)OC₂H₅ | CHF₂ |
| 191 | F | Cl | CH(CH₃)OCH₂CH=CH₂ | CHF₂ |
| 192 | F | Cl | CH(C₂H₅)OCH₃ | CHF₂ |
| 193 | F | Cl | CH(CH₃)SCH₃ | CHF₂ |
| 194 | F | Cl | CH(CH₃)SC₂H₅ | CHF₂ |
| 195 | F | Cl | CH(CH₃)S(O)C₂H₅ | CHF₂ |
| 196 | F | Cl | CH(CH₃)S(O)₂C₂H₅ | CHF₂ |
| 197 | F | Br | CH(CH₃)OCH₃ | CHF₂ |
| 198 | F | CF₃ | CH(CH₃)OCH₃ | CHF₂ |
| 199 | Cl | CF₃ | CH(CH₃)OCH₃ | CHF₂ |
| 200 | F | NO₂ | CH(CH₃)OCH₃ | CHF₂ |

TABLE 1-continued

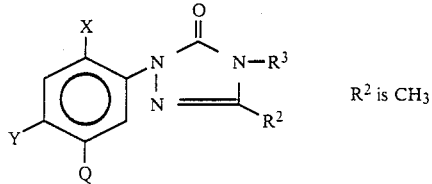

R² is CH₃

| Cmpd. No. | X | Y | Q | R³ |
|---|---|---|---|---|
| 201 | Cl | NO₂ | CH(CH₃)OCH₃ | CHF₂ |

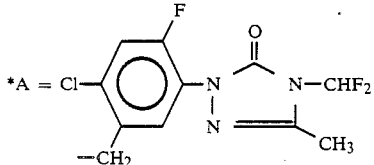

rmk-6/md

TABLE 2

| Cmpd. No. | Name | Empirical Formula/ Melting Point (°C.) | Elemental Analyses C | H | N |
|---|---|---|---|---|---|
| 1 | 1-(5-aminomethyl-4-chloro-2-fluorophenyl)-4-difluoromethyl-4,5-dihydro-3-methyl-1,2,4-triazol-5(H)—one | C₁₁H₁₀ClF₃N₄O 89–90 | C 43.08 F 42.91 | 3.29 3.02 | 18.27 18.00 |
| 2 | 1-[4-chloro-2-fluoro-5-(2-propynylaminomethyl)phenyl]-4-difluoromethyl-4,5-dihydro-3-methyl-1,2,4-triazol-5(H)—one | C₁₄H₁₂ClF₃N₄O oil | C 48.78 F 48.03 | 3.51 3.28 | 16.25 15.30 |
| 3 | 1-[4-chloro-5-[1-(ethoxycarbonyl)-ethylaminomethyl]-2-fluorophenyl]-4-difluoromethyl-4,5-dihydro-3-methyl-1,2,4-triazol-5-(H)—one | C₁₆H₁₈ClF₃N₄O oil | C 47.24 F 47.59 | 4.46 4.43 | 13.77 14.01 |
| 4 | 1-(4-chloro-2-fluoro-5-methoxyaminomethylphenyl)-4-difluoromethyl-4,5-dihydro-3-methyl-1,2,4-triazol-5-(H)—one | C₁₂H₁₂ClF₃N₄O₂ oil | | | |
| 5 | 1-(5-acetylaminomethyl-4-chloro-2-fluorophenyl)-4-difluoromethyl-4,5-dihydro-3-methyl-1,2,4-triazol-5-(H)—one | C₁₃H₁₂ClF₃N₄O₂ 119–121 | C 44.78 F 44.63 | 3.47 3.8 | 16.07 15.77 |
| 6 | 1-(4-chloro-5-ethoxycarbonylaminomethyl-2-fluorophenyl)-4-difluoromethyl-4,5-dihydro-3-methyl-1,2,4-triazol-5-(H)—one | C₁₄H₁₄ClF₃N₄O₃ oil | C 44.40 F 44.51 | 3.73 3.90 | 14.79 14.59 |
| 7 | 1-(4-chloro-2-fluoro-5-methylaminocarbonylaminomethylphenyl)-4-difluoromethyl-4,5-dihydro-3-methyl-1,2,4-triazol-5(H)—one | C₁₃H₁₃ClF₃N₅O₂ 175–177 | C 42.93 F 43.06 | 3.60 3.80 | 19.25 19.15 |
| 8 | 1-(4-chloro-2-fluoro-5-methylsulfonylaminomethylphenyl)-4-difluoromethyl-4,5-dihydro-3-methyl-1,2,4-triazol-5(H)—one | C₁₂H₁₂ClF₃N₄O₃S 120–122 | C 37.46 F 37.39 | 3.14 2.95 | 14.56 13.88 |
| 9 | 1-(4-chloro-5-diethylaminomethyl-2-fluorophenyl)-4-difluoromethyl-4,5-dihydro-3-methyl-1,2,4-triazol-5(H)—one | C₁₅H₁₈ClF₃N₄O oil | C 49.66 F 49.68 | 5.00 4.81 | 15.44 15.15 |
| 10 | 1-(4-chloro-2-fluoro-5-morpholinomethylphenyl)-4-difluoromethyl-4,5-dihydro-3-methyl-1,2,4-triazol-5(H)—one | C₁₅H₁₆ClF₃N₄O₂ 95–98 | C 47.81 F 47.51 | 4.28 4.15 | 14.87 14.64 |
| 11 | 1-[5-(N-acetyl-N—methoxyaminomethyl)-4-chloro-2-fluorophenyl]-4-difluoromethyl-4,5-dihydro-3-methyl-1,2,4-triazol-5(H)—one | C₁₄H₁₄ClF₃N₄O₃ 74–78 | C 44.40 F 44.10 | 3.73 3.98 | 14.79 14.48 |
| 12 | 1-[4-chloro-2-fluoro-5-(N—fluoroacetyl-N—methoxyaminomethyl)phenyl]-4-difluoromethyl-4,5-dihydro-3-methyl-1,2,4-triazol-5(H)—one | C₁₄H₁₃ClF₄N₄O₃ oil | C 42.38 F 42.65 | 3.30 3.25 | 14.12 14.50 |
| 13 | 1-[4-chloro-5-(N—chloroacetyl-N—methoxyaminomethyl)phenyl]-4-difluoromethyl-4,5-dihydro-3-methyl-1,2,4-triazol-5(H)—one | C₁₄H₁₃Cl₂F₃N₄O₃ oil | C 40.70 F 39.36 | 3.17 2.98 | 13.56 11.05 |
| 14 | 1-[4-chloro-5-(N—difluoroacetyl-N—methoxyaminomethyl)phenyl]-4-difluoromethyl-4,5-dihydro-3-methyl-1,2,4-triazol-5(H)—one | C₁₄H₁₂ClF₅N₄O₃ oil | C 40.55 F 41.24 | 2.92 3.12 | 13.51 13.83 |

TABLE 2-continued

| Cmpd. No. | Name | Empirical Formula/ Melting Point (°C.) | | Elemental Analyses C | H | N |
|---|---|---|---|---|---|---|
| 15 | 1-[4-chloro-2-fluoro-5-(N—trifluoro-acetyl-N—methoxyaminomethyl)phenyl]-4-difluoromethyl-4,5-dihydro-3-methyl-1,2,4-triazol-5(H)—one | $C_{14}H_{11}ClF_6N_4O_3$ 96–99 | C F | 38.86 38.50 | 2.56 2.39 | 12.95 12.79 |
| 16 | 1-[4-chloro-5-[N—(1,1-dimethylethyl-carbonyl)-N—methoxyaminomethyl]-2-fluorophenyl]-4-difluoromethyl-4,5-dihydro-3-methyl-1,2,4-triazol-5(H)—one | $C_{17}H_{20}ClF_3N_4O_3$ 98–100 | C F | 48.52 47.62 | 4.79 4.41 | 13.31 13.29 |
| 17 | 1-[4-chloro-5-[N—(2-chloro-1,1-di-methylethylcarbonyl)-N—methoxyamino-methyl]-2-fluorophenyl]-4-difluoro-methyl-4,5-dihydro-3-methyl-1,2,4-triazol-5(H)—one | $C_{17}H_{19}Cl_2F_3N_4O_3$ 65–66 | C F | 44.85 44.98 | 4.21 4.26 | 12.31 12.15 |
| 18 | 1-[4-chloro-5-(N—ethenylcarbonyl-N—methoxyaminomethyl)-2-fluoro-phenyl]-4-difluoromethyl-4,5-dihydro-3-methyl-1,2,4-triazol-5(H)—one | $C_{15}H_{14}ClF_3N_4O_3$ 110–112 | C F | 46.11 46.29 | 3.61 3.64 | 14.34 14.04 |
| 19 | 1-[4-chloro-5-[(4,4-dimethyl-3-oxo-isoxazolidin-2-yl)methyl]-2-fluoro-phenyl]-4,5-dihydro-3-methyl-1,2,4-triazol-5(H)—one | $C_{15}H_{16}ClFN_4O_3$ oil | C F | 50.78 51.57 | 4.55 4.75 | 15.79 14.21 |
| 20 | 1-[4-chloro-5-[(4,4-dimethyl-3-oxo-isoxazolidin-2-yl)methyl]-2-fluoro-phenyl]-4-difluoromethyl-4,5-dihydro-3-methyl-1,2,4-triazol-5(H)—one | $C_{15}H_{16}ClF_3N_4O_3$ 97–100 | | | | |
| 21 | 1-[2,4-dichloro-5-[(4,4-dimethyl-3-oxo-isoxazolidin-2-yl)methyl]phenyl]-4,5-di-hydro-1,2,4-triazol-5(H)—one | $C_{15}H_{16}Cl_2N_4O_3$ foam | C F | 48.53 48.48 | 4.34 4.40 | 15.09 14.05 |
| 22 | 1-[2,4-dichloro-5-[(4,4-dimethyl-3-oxo-isoxazolidin-2-yl)methyl]phenyl]-4-di-fluoromethyl-4,5-dihydro-3-methyl-1,2,4-triazol-5(H)—one | $C_{16}H_{16}Cl_2F_2N_4O_3$ 155–156 | C F | 45.62 45.68 | 3.83 3.65 | 13.30 12.99 |
| 23 | 1-[2-chloro-5-[(4,4-dimethyl-3-oxo-isoxazolidin-2-yl)methyl]-4-fluoro-phenyl]-4,5-dihydro-3-methyl-1,2,4-triazol-5(H)—one | $C_{15}H_{16}ClFN_4O_3$ 153–155 | C F | 50.78 50.48 | 4.55 4.32 | 15.79 15.63 |
| 24 | 1-[2,4-dichloro-5-[(4,4-dimethyl-3-oxo-isoxazolidin-2-yl)methyl]phenyl]-4-ethyl-4,5-dihydro-3-methyl-1,2,4-triazol-5(H)—one | $C_{17}H_{20}Cl_2N_4O_3$ oil | C F | 51.14 50.82 | 5.05 5.19 | 14.03 13.10 |
| 25 | 1-[2,4-dichloro-5-[(4,4-dimethyl-3-oxo-isoxazolidin-2-yl)methyl]phenyl]-4,5-di-hydro-3-methyl-4-propyl-1,2,4-triazol-5(H)—one | $C_{18}H_{22}Cl_2N_4O_3$ oil | C F | 52.31 52.00 | 5.37 5.42 | 13.56 13.31 |
| 26 | 1-[4-chloro-5-[(4,4-dimethyl-3-oxo-isoxazolidin-2-yl)methyl]-2-fluorophenyl]-4,5-dihydro-3-methyl-4-(2-propenyl)-1,2,4-triazol-5(H)—one | $C_{17}H_{20}ClFN_4O_3$ oil | | | | |
| 27 | 1-[2,4-dichloro-5-[(4,4-dimethyl-3-oxo-isoxazolidin-2-yl)methyl]-4,5-di-hydro-3-methyl-4-(2-propenyl)-1,2,4-triazol-5(H)—one | $C_{18}H_{20}Cl_2N_4O_3$ oil | C F | 52.56 52.52 | 4.90 4.87 | 13.62 13.69 |
| 28 | 1-[2,4-dichloro-5-[(4,4-dimethyl-3-oxo-isoxazolidin-2-yl)methyl]phenyl]-4,5-di-hydro-3-methyl-4-(2-propynyl)-1,2,4-triazol-5(H)—one | $C_{18}H_{18}Cl_2N_4O_3$ oil | C F | 52.82 52.48 | 4.43 4.81 | 13.69 12.16 |
| 29 | 1-[2,4-dichloro-5-[(4,4-dimethyl-3-oxo-isoxazolidin-2-yl)methyl]phenyl]-4-cyanomethyl-4,5-dihydro-3-methyl-1,2,4-triazol-5(H)—one | $C_{17}H_{17}Cl_2N_5O_3$ oil | C F | 49.77 50.16 | 4.18 4.36 | 17.07 16.18 |
| 30 | 1-[2,4-dichloro-5-[(4,4-dimethyl-3-oxo-isoxazolidin-2-yl)methyl]phenyl]-4-(ethoxycarbonylmethyl)-4,5-dihydro-3-methyl-1,2,4-triazol-5(H)—one | $C_{19}H_{22}Cl_2N_4O_5$ oil | C F | 49.90 50.86 | 4.85 4.94 | 12.25 12.19 |
| 31 | 1-[2,4-dichloro-5-[(4,4-dimethyl-3-oxo-isoxazolidin-2-yl)methyl]phenyl]-4,5-dihydro-3-methyl-4-phenylmethyl-1,2,4-triazol-5(H)—one | $C_{22}H_{22}Cl_2N_4O_3$ oil | C F | 57.28 58.33 | 4.81 5.48 | 12.14 11.39 |
| 32 | 1-[2,4-dichloro-5-[(4,4-dimethyl-3-oxo-isoxazolidin-2-yl)methyl]phenyl]-4-[(2-chlorophenyl)methyl]-4,5-dihydro-3-methyl-1,2,4-triazol-5(H)—one | $C_{22}H_{21}Cl_3N_4O_3$ oil | C F | 53.30 46.62 | 4.27 3.77 | 11.30 9.37 |
| 33 | 1-[4-chloro-5-[(4-methyl-4-methylthio 3-oxo-3,4,5,6-tetrahydro-1,2-oxazin-2-yl)methyl]-2-fluorophenyl]-4-difluoro-methyl-4,5-dihydro-3-methyl-1,2,4-tri-azol-5(H)—one | $C_{17}H_{18}ClF_3N_4O_3S$ 102–104 | C F | 45.29 45.44 | 4.02 4.02 | 12.43 2.70 |
| 34 | 1-[4-chloro-2-fluoro-5-[(N—methoxy-N—methylsulfonyl)aminomethyl]phenyl]-4-difluoromethyl-4,5-dihydro- | $C_{13}H_{14}ClN_4F_3O_4S$ oil | C F | 37.64 38.35 | 3.40 3.57 | 13.51 12.57 |

TABLE 2-continued

| Cmpd. No. | Name | Empirical Formula/ Melting Point (°C.) | Elemental Analyses | | |
|---|---|---|---|---|---|
| | | | C | H | N |
| | 3-methyl-1,2,4-triazol-5(H)—one | | | | |
| 35 | 1-[4-chloro-2-fluoro-5-[(N—methoxy-N—trifluoromethylsulfonyl)aminomethyl]phenyl]-4-difluoromethyl-4,5-dihydro-3-methyl-1,2,4-triazol-5(H)—one | $C_{13}H_{11}ClF_6N_4O_4S$ oil | C 33.31 F 33.43 | 2.37 2.19 | 11.95 11.72 |
| 36 | 1-[4-chloro-2-fluoro-5-[[N—methoxy-N—(2-chlorophenylsulfonyl)]aminomethyl]phenyl]-4-difluoromethyl-4,5-dihydro-3-methyl-1,2,4-triazol-5(H)—one | $C_{18}H_{15}Cl_2F_3N_4O_4S$ oil | C 42.28 F 42.47 | 2.96 3.09 | 10.96 10.73 |
| 37 | 1-[4-chloro-2-fluoro-5-[[N—methoxy-N—(4-methoxyphenylsulfonyl)]aminomethyl]phenyl]-4-difluoromethyl-4,5-dihydro-3-methyl-1,2,4-triazol-5(H)—one | $C_{19}H_{18}ClF_3N_4O_5S$ oil | C 45.02 F 45.18 | 3.58 3.80 | 11.05 10.89 |
| 38 | 1-[4-chloro-2-fluoro-5-[[(N—ethoxy-N—(2-methoxycarbonylphenylsulfonyl))]-aminomethyl]phenyl]-4-difluoromethyl-4,5-dihydro-3-methyl-1,2,4-triazol-5(H)—one | $C_{20}H_{18}ClF_3N_4O_6S$ foam | C 44.91 F 44.90 | 3.39 3.65 | 10.47 10.55 |
| 39 | 1-[2-chloro-5-(5,5-dimethyl-4(3H)—oxo-dihydro-2H—1,3-oxazin-2-yl)-4-fluorophenyl]-4,5-dihydro-3-methyl-1,2,4-triazol-5(H)—one | $C_{15}H_{16}ClFN_4O_3$ 145–147 | C 50.78 F 51.30 | 4.55 4.75 | 15.79 14.40 |
| 40 | 1-[2-chloro-5-(5,5-dimethyl-4(3H)—oxo-dihydro-2H—1,3-oxazin-2-yl)-4-fluorophenyl]-4-difluoromethyl-4,5-dihydro-3-methyl-1,2,4-triazol-5(H)—one | $C_{16}H_{16}ClF_3N_4O_3$ foam | C 47.48 F 47.47 | 3.98 3.80 | 13.84 13.21 |
| 41 | 1-[2,4-dichloro-5-(3,5,5-trimethyl-4(3H)—oxodihydro-2H—1,3-oxazin-2-yl)-phenyl]-4,5-dihydro-3,4-dimethyl-1,2,4-triazol-5(H)—one | $C_{17}H_{20}Cl_2N_4O_3$ 175–178 | C 51.14 F 51.11 | 5.05 4.90 | 14.03 13.72 |
| 42 | 1-[2,4-dichloro-5-(5,5-dimethyl-4(3H)—oxodihydro-2H—1,3-oxazin-2-yl)phenyl]-4-difluoromethyl-4,5-dihydro-3-methyl-1,2,4-triazol-5(H)—one | $C_{16}H_{16}Cl_2F_2N_4O_3$ 81–85 | C 45.62 F 46.44 | 3.83 4.37 | 13.30 11.14 |
| 43 | 1-[2,4-dichloro-5-[5,5-dimethyl-3-(2-propenyl)-4(3H)—oxodihydro-2H—1,3-oxazin-2-yl]phenyl]-4,5-dihydro-3-methyl-4-(2-propenyl)-1,2,4-triazol-5(H)—one | $C_{21}H_{24}Cl_2N_4O_3$ 118–121 | C 55.88 F 55.73 | 5.36 5.35 | 12.41 11.93 |
| 45 | 1-(4-chloro-2-fluoro-5-phthalimido-methylphenyl)-4-difluoromethyl-4,5-dihydro-3-methyl-1,2,4-triazol-5(H)—one | $C_{19}H_{12}ClF_3N_4O_3$ 152–154 | C 52.25 F 52.10 | 2.77 2.85 | 12.83 12.60 |
| 46 | bis[[4-chloro-2-fluoro-5-(4-difluoromethyl-4,5-dihydro-3-methyl-1,2,4-triazol-5(H)—one-1-yl)phenyl]methyl]amine | $C_{22}H_{17}Cl_2F_6N_7O_4$ 142–144 | C 44.31 F 44.69 | 2.87 2.86 | 16.44 16.08 |
| 47 | N,N—bis[[4-chloro-2-fluoro-5-(4-difluoromethyl-4,5-dihydro-3-methyl-1,2,4-triazol-5(H)—one-1-yl)phenyl]methyl]acetamide | $C_{24}H_{19}Cl_2F_6N_7O_3$ foam | C 45.16 F 44.85 | 3.00 2.72 | 15.36 15.09 |
| 48 | bis[[4-chloro-2-fluoro-5-(4-difluoromethyl-4,5-dihydro-3-methyl-1,2,4-triazol-5(H)—one-1-yl)phenyl]methyl]-methylsulfonylamine | $C_{23}H_{19}Cl_2F_6N_7O_4S$ 192–193 | C 40.96 F 41.24 | 2.83 2.94 | 14.54 14.18 |
| 49 | tris[[4-chloro-2-fluoro-5-(4-difluoromethyl-4,5-dihydro-3-methyl-1,2,4-triazol-5(H)—one-1-yl)phenyl]methyl]-amine | $C_{33}H_{24}Cl_3F_9N_{10}O_3$ 159–161 | C 44.74 F 45.37 | 2.73 2.97 | 15.81 15.11 |
| 50 | 1-(4-chloro-2-fluoro-5-hydroxymethyl-phenyl)-4-difluoromethyl-4,5-dihydro-3-methyl-1,2,4-triazol-5(H)—one | $C_{11}H_9ClF_3N_3O_2$ solid | | | |
| 51 | 1-(4-chloro-2-fluoro-5-methoxymethyl-phenyl)-4-difluoromethyl-4,5-dihydro-3-methyl-1,2,4-triazol-5(H)—one | $C_{12}H_{11}ClF_3N_3O_2$ oil | C 44.81 F 44.73 | 3.45 3.18 | 13.06 12.95 |
| 52 | 1-(4-chloro-5-ethoxymethyl-2-fluoro-phenyl)-4-difluoromethyl-4,5-dihydro-3-methyl-1,2,4-triazol-5(H)—one | $C_{13}H_{13}ClF_3N_3O_2$ oil | C 46.50 F 46.38 | 3.87 3.65 | 12.52 12.30 |
| 53 | 1-[4-chloro-2-fluoro-5-(2-fluoroethoxymethyl)phenyl]-4-difluoromethyl-4,5-dihydro-3-methyl-1,2,4-triazol-5(H)—one | $C_{13}H_{12}ClF_4N_3O_2$ oil | C 44.15 F 44.11 | 3.42 3.24 | 11.88 11.80 |
| 54 | 1-[4-chloro-2-fluoro-5-(1-methyl-ethoxymethyl)phenyl]-4-difluoromethyl-4,5-dihydro-3-methyl-1,2,4-triazol-5(H)—one | $C_{14}H_{15}ClF_3N_3O_2$ oil | C 48.08 F 47.94 | 4.32 4.11 | 12.01 11.98 |
| 55 | 1-[4-chloro-2-fluoro-5-(1-fluoromethyl-2-fluoroethoxymethyl)phenyl]- | $C_{14}H_{13}ClF_5N_3O_2$ 80–82 | C 43.59 F 43.89 | 3.40 3.65 | 10.89 10.82 |

TABLE 2-continued

| Cmpd. No. | Name | Empirical Formula/ Melting Point (°C.) | | C | H | N |
|---|---|---|---|---|---|---|
| | 4-difluoromethyl-4,5-dihydro-3-methyl-1,2,4-triazol-5(H)—one | | | | | |
| 56 | 1-(4-chloro-5-cyclopropylmethoxymethyl-2-fluorophenyl)-4-difluoromethyl-4,5-dihydro-3-methyl-1,2,4-triazol-5(H)—one | $C_{15}H_{15}ClF_3N_3O_2$ oil | C F | 49.80 49.86 | 4.18 4.20 | 11.62 11.43 |
| 57 | 1-[4-chloro-2-fluoro-5-(2-propenyloxymethyl)phenyl]-4-difluoromethyl-4,5-dihydro-3-methyl-1,2,4-triazol-5(H)—one | $C_{14}H_{13}ClF_3N_3O_2$ oil | C F | 48.36 47.86 | 3.77 3.52 | 12.08 12.00 |
| 58 | 1-[4-chloro-2-fluoro-5-(2-propynyloxymethyl)phenyl]-4-difluoromethyl-4,5-dihydro-3-methyl-1,2,4-triazol-5(H)—one | $C_{14}H_{11}ClF_3N_3O_2$ oil | C F | 48.64 49.14 | 3.21 3.21 | 12.16 11.78 |
| 59 | 1-[2,4-dichloro-5-(2-propynyloxymethyl)phenyl]-4-difluoromethyl-4,5-dihydro-3-methyl-1,2,4-triazol-5(H)—one | $C_{14}H_{11}Cl_2F_2N_3O_2$ oil | C F | 46.43 47.12 | 3.06 3.14 | 11.60 10.61 |
| 60 | 1-(4-chloro-2-fluoro-5-methoxymethoxymethylphenyl)-4-difluoromethyl-4,5-dihydro-3-methyl-1,2,4-triazol-5(H)—one | $C_{13}H_{13}ClF_3N_3O_3$ oil | C F | 44.40 44.19 | 3.73 3.53 | 11.95 11.65 |
| 61 | 1-[4-chloro-2-fluoro-5-[(2-methoxyethoxy)methyl]phenyl]-4-difluoromethyl-4,5-dihydro-3-methyl-1,2,4-triazol-5(H)—one | $C_{14}H_{15}ClF_3N_3O_3$ oil | C F | 45.98 45.99 | 4.13 3.85 | 11.49 11.12 |
| 62 | 1-[4-chloro-2-fluoro-5-[(tetrahydropyran-2-yl)oxymethyl]phenyl]-4-difluoromethyl-4,5-dihydro-3-methyl-1,2,4-triazol-5(H)—one | $C_{16}H_{17}ClF_3N_3O_3$ 115–117 | C F | 49.05 50.05 | 4.37 4.27 | 10.73 10.11 |
| 63 | 1-[4-chloro-2-fluoro-5-[(tetrahydrofuran-3-yl)oxymethyl]phenyl]-4-difluoromethyl-4,5-dihydro-3-methyl-1,2,4-triazol-5(H)—one | $C_{15}H_{15}ClF_3N_3O_2$ oil | C F | 47.69 47.74 | 4.00 4.30 | 11.12 10.86 |
| 64 | 1-[4-chloro-2-fluoro-5-(methylcarbonyloxymethyl)phenyl]-4-difluoromethyl-4,5-dihydro-3-methyl-1,2,4-triazol-5(H)—one | $C_{13}H_{11}ClF_3N_3O_3$ oil | | | | |
| 65 | 1-[4-chloro-2-fluoro-5-(fluoromethylcarbonyloxymethyl)phenyl]-4-difluoromethyl-4,5-dihydro-3-methyl-1,2,4-triazol-5(H)—one | $C_{13}H_{10}ClF_4N_3O_3$ 84–86 | C F | 42.47 42.37 | 2.74 2.68 | 11.43 11.58 |
| 66 | 1-[4-chloro-5-[(2-chloroethyl)carbonyloxymethyl]-2-fluorophenyl]-4-difluoromethyl-4,5-dihydro-3-methyl-1,2,4-triazol-5(H)—one | $C_{14}H_{12}Cl_2F_3N_3O_3$ oil | C F | 42.23 42.50 | 3.04 2.95 | 10.55 10.21 |
| 67 | 1-[4-chloro-5-(ethoxycarbonylmethoxymethyl)-2-fluorophenyl]-4-difluoromethyl-4,5-dihydro-3-methyl-1,2,4-triazol-5(H)—one | $C_{15}H_{15}ClF_3N_3O_4$ oil | C F | 45.76 45.65 | 3.84 3.59 | 10.67 10.57 |
| 68 | 1-(4-chloro-2-fluoro-5-nitrooxymethylphenyl)-4-difluoromethyl-4,5-dihydro-3-methyl-1,2,4-triazol-5(H)—one | $C_{11}H_{18}ClF_3N_4O_4$ 104–106 | C F | 37.46 38.11 | 2.29 2.35 | 15.88 15.62 |
| 69 | 1-(4-chloro-2-fluoro-5-phenoxymethylphenyl)-4-difluoromethyl-4,5-dihydro-3-methyl-1,2,4-triazol-5(H)—one | $C_{17}H_{13}ClF_3N_3O_2$ 95–97 | C F | 53.21 51.58 | 3.41 3.27 | 10.95 10.87 |
| 70 | 1-[4-chloro-2-fluoro-5-[(2-chloro-4-trifluoromethylphenoxy)methyl]phenyl]-4-difluoromethyl-4,5-dihydro-3-methyl-1,2,4-triazol-5(H)—one | $C_{18}H_{11}Cl_2F_6N_3O_2$ 143–144 | C F | 44.47 44.74 | 2.28 2.17 | 8.64 8.49 |
| 71 | 1-[4-chloro-2-fluoro-5-(phenylmethoxymethyl)phenyl]-4-difluoromethyl-4,5-dihydro-3-methyl-1,2,4-triazol-5(H)—one | $C_{18}H_{15}ClF_3N_3O_2$ oil | C F | 54.35 53.40 | 3.80 3.79 | 10.56 10.52 |
| 72 | 1-(4-chloro-2-fluoro-5-methylthiomethylphenyl)-4-difluoromethyl-4,5-dihydro-3-methyl-1,2,4-triazol-5(H)—one | $C_{12}H_{11}ClF_3N_3OS$ 116–119 | C F | 42.67 42.53 | 3.28 3.02 | 12.44 12.48 |
| 73 | 1-(4-chloro-5-ethylthiomethyl-2-fluorophenyl)-4-difluoromethyl-4,5-dihydro-3-methyl-1,2,4-triazol-5(H)—one | $C_{13}H_{13}ClF_3N_3OS$ oil | C F | 44.39 44.96 | 3.72 3.60 | 11.94 11.65 |
| 74 | 1-[4-chloro-2-fluoro-5-[(2-propenylthio)methyl]phenyl]-4-difluoromethyl-4,5-dihydro-3-methyl-1,2,4-triazol-5(H)—one | $C_{14}H_{13}ClF_3N_3OS$ 71–74 | C F | 46.22 46.06 | 3.60 3.32 | 11.55 11.57 |
| 75 | 1-[4-chloro-2-fluoro-5-[(methoxycarbonylmethyl)thiomethyl]phenyl]-4-difluoromethyl-4,5-dihydro-3-methyl-1,2,4-triazol-5(H)—one | $C_{14}H_{13}ClF_3N_3O_3S$ oil | | | | |
| 76 | 1-(4-chloro-5-thiocyanatomethyl-2-fluorophenyl)-4-difluoromethyl-4,5-dihydro- | $C_{12}H_8ClF_3N_4OS$ | | | | |

TABLE 2-continued

| Cmpd. No. | Name | Empirical Formula/ Melting Point (°C.) | Elemental Analyses C | H | N |
|---|---|---|---|---|---|
| | 3-methyl-1,2,4-triazol-5(H)—one | | | | |
| 77 | 1-(4-chloro-5-ethylsulfinylmethyl-2-fluorophenyl)-4-difluoromethyl-4,5-dihydro-3-methyl-1,2,4-triazol-5(H)—one | $C_{13}H_{13}ClF_3N_3O_2S$ 104–108 | C 42.46 F 41.15 | 3.56 3.41 | 11.43 11.00 |
| 78 | 1-[4-chloro-2-fluoro-5-(2-propenyl-sulfinylmethyl)phenyl]-4-difluoromethyl-4,5-dihydro-3-methyl-1,2,4-triazol-5(H)—one | $C_{14}H_{13}ClF_3N_3O_2S$ oil | C 44.28 F 44.65 | 3.45 3.11 | 11.06 10.35 |
| 79 | 1-(4-chloro-5-ethylsulfonylmethyl-2-fluorophenyl)-4-difluoromethyl-4,5-dihydro-3-methyl-1,2,4-triazol-5(H)—one | $C_{13}H_{13}ClF_3N_3O_3S$ 167–169 | C 40.69 F 41.00 | 3.41 3.60 | 10.95 10.81 |
| 80 | 1-[4-chloro-2-fluoro-5-(2-propenyl-sulfonylmethyl)phenyl]-4-difluoromethyl-4,5-dihydro-3-methyl-1,2,4-triazol-5(H)—one | $C_{14}H_{13}ClF_3N_3O_3S$ 160–165 | C 42.49 F 44.56 | 3.31 2.96 | 10.62 10.52 |
| 81 | 1-(4-chloro-2-fluoro-5-hydroxyimino-methylphenyl)-4-difluoromethyl-4,5-dihydro-3-methyl-1,2,4-triazol-5(H)—one | $C_{11}H_{10}ClF_3N_4O_3$ 125–127 | C 39.01 F 39.31 | 2.98 3.20 | 16.54 16.11 |
| 82 | 1-(4-chloro-2-fluoro-5-methoxyimino-methylphenyl)-4-difluoromethyl-4,5-dihydro-3-methyl-1,2,4-triazol-5(H)—one | $C_{12}H_{10}ClF_3N_4O_2$ 90–92 | C 43.07 F 42.61 | 3.01 2.80 | 16.74 16.28 |
| 83 | 1-(2-chloro-5-acetoxyiminomethyl-4-fluorophenyl)-4-difluoromethyl-4,5-dihydro-3-methyl-1,2,4-triazol-5(H)—one | $C_{13}H_{10}ClF_3N_4O_3$ oil | C 43.05 F 43.55 | 2.78 3.24 | 15.45 15.38 |
| 84 | 1-[4-chloro-2-fluoro-5-[dimethyl-(1,1-dimethylethyl)silyloxyimino-methyl]phenyl]-4-difluoromethyl-4,5-dihydro-3-methyl-1,2,4-triazol-5(H)—one | $C_{17}H_{22}ClF_3N_4O_2Si$ 80–83 | C 46.95 F 46.66 | 5.10 4.95 | 12.88 12.69 |

TABLE 3
PREEMERGENCE HERBICIDAL ACTIVITY

| Compound | 1 | 2 | 3 | 5 | 6 | 7 | 8 |
|---|---|---|---|---|---|---|---|
| Rate (kg/ha) | 1.0 | 2.0 | 1.0 | 0.5 | 1.0 | 1.0 | 0.5 |
| | % C | % C | % C | % C | % C | % C | % C |
| 70 | 60 | 60 | 95 | 80 | 95 | 90 | |
| Soybean | 70 | 70 | 40 | 100 | 95 | 95 | 100 |
| Field Corn | 95 | 80 | 90 | 100 | 100 | 100 | 100 |
| Rice | 95 | 90 | 80 | 100 | 100 | 100 | 100 |
| Wheat | 95 | 90 | 30 | 100 | 100 | 100 | 100 |
| Bindweed | 100 | 100 | 100 | 100 | 100 | 100 | 80 |
| Morningglory | 90 | 100 | 90 | 100 | 95 | 100 | 100 |
| Velvetleaf | 100 | 100 | 100 | 100 | 100 | 100 | 100 |
| Barnyardgrass | 100 | 100 | 100 | 100 | 100 | 100 | 100 |
| Green Foxtail | 90 | 100 | 95 | 100 | 100 | 100 | 100 |
| Johnsongrass | 95 | 100 | 95 | 100 | 100 | 100 | 100 |
| Yellow Nutsedge | — | — | — | — | — | — | — |

| Compound | 9 | 10 | 11 | 12 | 13 | 14 | 15 |
|---|---|---|---|---|---|---|---|
| Rate (kg/ha) | 2.0 | 2.0 | 0.5 | 1.0 | 1.0 | 1.0 | 1.0 |
| | % C | % C | % C | % C | % C | % C | % C |
| Cotton | 0 | 90 | 50 | 100 | 70 | 30 | 10 |
| Soybean | 10 | 100 | 100 | 95 | 70 | 100 | 80 |
| Field Corn | 20 | 100 | 100 | 100 | 100 | 100 | 100 |
| Rice | 30 | 100 | 90 | 100 | 95 | 100 | 95 |
| Wheat | 10 | 100 | 100 | 100 | 100 | 100 | 100 |
| Bindweed | 20 | 100 | 100 | 100 | 100 | 80 | 50 |
| Morningglory | 80 | 100 | 90 | 100 | 100 | 100 | 100 |
| Velvetleaf | 100 | 100 | 100 | 100 | 100 | 100 | 100 |
| Barnyardgrass | 90 | 100 | 100 | 100 | 100 | 100 | 100 |
| Green Foxtail | 100 | 100 | 100 | 100 | 100 | 100 | 100 |
| Johnsongrass | 70 | 100 | 100 | 100 | 100 | 100 | 100 |
| Yellow Nutsedge | 20 | — | 70 | — | — | — | — |

TABLE 3-continued
PREEMERGENCE HERBICIDAL ACTIVITY

| Compound | 16 | 17 | 18 | 19 | 20 | 21 | 22 |
|---|---|---|---|---|---|---|---|
| Rate (kg/ha) | 1.0 | 1.0 | 0.5 | 8.0 | 1.0 | 8.0 | 8.0 |
| | % C | % C | % C | % C | % C | % K | % K |
| Cotton | 20 | 10 | 40 | 10 | 90 | — | 100 |
| Soybean | 50 | 30 | 70 | 10 | 100 | 0 | 100 |
| Field Corn | 90 | 100 | 100 | 30 | 100 | 0 | 100 |
| Rice | 90 | 40 | 100 | — | — | — | 100 |
| Wheat | 60 | 10 | 90 | 20 | 100 | 0 | 100 |
| Bindweed | 40 | 0 | 100 | 30 | — | 0 | 100 |
| Morningglory | 50 | 0 | 100 | 20 | 100 | 0 | 100 |
| Velvetleaf | 100 | 100 | 100 | 30 | 100 | 0 | 100 |
| Barnyardgrass | 100 | 100 | 100 | 60 | 100 | 100 | 100 |
| Green Foxtail | 100 | 80 | 100 | 20 | 100 | 0 | 100 |
| Johnsongrass | 100 | 90 | 100 | 10 | 100 | 0 | 100 |
| Yellow Nutsedge | 10 | 0 | — | — | 90 | — | 100 |

| Compound | 23 | 24 | 25 | 26 | 27 | 28 | 29 |
|---|---|---|---|---|---|---|---|
| Rate (kg/ha) | 8.0 | 8.0 | 8.0 | 1.0 | 8.0 | 8.0 | 8.0 |
| | % C | % C | % K | % C | % K | % K | % K |
| Cotton | 10 | 80 | 30 | 50 | 50 | 20 | 0 |
| Soybean | 10 | 100 | 70 | 80 | 100 | 40 | 0 |
| Field Corn | 30 | 100 | 100 | 100 | 100 | 100 | 100 |
| Rice | — | — | 90 | 90 | 100 | 100 | 0 |
| Wheat | 0 | 95 | 95 | 60 | 95 | 70 | 0 |
| Bindweed | 0 | 0 | 30 | 20 | 100 | 40 | 90 |
| Morningglory | 10 | 0 | 0 | 80 | 100 | 30 | 20 |
| Velvetleaf | 0 | 0 | 100 | 100 | 100 | 100 | 100 |
| Barnyardgrass | 10 | 0 | 100 | 70 | 100 | 100 | 0 |
| Green Foxtail | 20 | 0 | 100 | 100 | 100 | 100 | 90 |
| Johnsongrass | 0 | 0 | 100 | 90 | 100 | 100 | 80 |
| Yellow Nutsedge | — | — | 0 | 40 | 0 | 0 | 0 |

| Compound | 30 | 31 | 32 | 34 | 35 | 36 | 37 |
|---|---|---|---|---|---|---|---|

TABLE 3-continued
PREEMERGENCE HERBICIDAL ACTIVITY

| | \multicolumn{7}{c}{Rate (kg/ha)} | | | | | | |
|---|---|---|---|---|---|---|---|
| | 8.0 % K | 8.0 % K | 4.0 % K | 8.0 % C | 1.0 % C | 1.0 % C | 1.0 % C |
| Cotton | 0 | 60 | 20 | 50 | 20 | 0 | 60 |
| Soybean | 0 | 70 | 0 | 80 | 10 | 0 | 30 |
| Field Corn | 0 | 60 | 0 | 0 | 70 | 10 | 40 |
| Rice | — | 0 | 0 | — | 20 | 30 | 30 |
| Wheat | 0 | 100 | 0 | 0 | 0 | 0 | 20 |
| Bindweed | 0 | 50 | 30 | 10 | 80 | 20 | 50 |
| Morningglory | 0 | 0 | 100 | 30 | 80 | 20 | 30 |
| Velvetleaf | 0 | 100 | 0 | 30 | 100 | 80 | 90 |
| Barnyardgrass | 0 | 100 | 90 | 30 | 100 | 30 | 60 |
| Green Foxtail | 0 | 100 | 100 | 0 | 95 | 0 | 80 |
| Johnsongrass | 0 | 100 | 70 | 0 | 90 | 10 | 60 |
| Yellow Nutsedge | — | 0 | 0 | — | — | — | — |

| | \multicolumn{7}{c}{Compound} | | | | | | |
|---|---|---|---|---|---|---|---|
| | 38 | 39 | 40 | 41 | 42 | 43 | 45 |
| | \multicolumn{7}{c}{Rate (kg/ha)} | | | | | | |
| | 1.0 % C | 8.0 % C | 2.0 % C | 8.0 % K | 8.0 % K | 8.0 % K | 1.0 % C |
| Cotton | 70 | 0 | 40 | 0 | 100 | 0 | 40 |
| Soybean | 50 | 0 | 40 | 0 | 100 | 0 | 30 |
| Field Corn | 80 | 30 | 30 | 60 | 100 | 100 | 80 |
| Rice | 50 | — | 20 | 0 | 100 | 20 | 60 |
| Wheat | 40 | 10 | 30 | 20 | 100 | 100 | 30 |
| Bindweed | 80 | 0 | 80 | 20 | 100 | 20 | 70 |
| Morningglory | 90 | 0 | 90 | 50 | 100 | 0 | 60 |
| Velvetleaf | 100 | 10 | 80 | 100 | 100 | 100 | 90 |
| Barnyardgrass | 80 | 0 | 30 | 30 | 100 | 100 | 95 |
| Green Foxtail | 100 | 0 | 40 | 100 | 100 | 100 | 100 |
| Johnsongrass | 95 | 0 | 40 | 60 | 100 | 100 | 80 |
| Yellow Nutsedge | — | — | 20 | 0 | 100 | 50 | — |

| | \multicolumn{7}{c}{Compound} | | | | | | |
|---|---|---|---|---|---|---|---|
| | 46 | 47 | 48 | 49 | 50 | 51 | 52 |
| | \multicolumn{7}{c}{Rate (kg/ha)} | | | | | | |
| | 8.0 % C | 2.0 % C | 8.0 % C | 8.0 % C | 2.0 % C | 1.0 % C | 1.0 % C |
| Cotton | 10 | 30 | 30 | 10 | 40 | 60 | 20 |
| Soybean | 10 | 20 | 20 | 20 | 100 | 100 | 100 |
| Field Corn | 70 | 40 | 30 | 40 | 100 | 100 | 100 |
| Rice | 80 | 30 | — | 50 | 100 | 100 | 100 |
| Wheat | 20 | 10 | 20 | 10 | 95 | 100 | 100 |
| Bindweed | 20 | 50 | 70 | 70 | 100 | 100 | 100 |
| Morningglory | 30 | 100 | 80 | 90 | 100 | 100 | 100 |
| Velvetleaf | 100 | 100 | 60 | 100 | 100 | 100 | 100 |
| Barnyardgrass | 95 | 30 | 80 | 100 | 100 | 100 | 100 |
| Green Foxtail | 20 | 60 | 60 | 100 | 100 | 100 | 100 |
| Johnsongrass | 90 | 60 | 60 | 95 | 95 | 100 | 100 |
| Yellow Nutsedge | — | — | — | — | — | — | — |

| | \multicolumn{7}{c}{Compound} | | | | | | |
|---|---|---|---|---|---|---|---|
| | 53 | 54 | 55 | 56 | 57 | 58 | 59 |
| | \multicolumn{7}{c}{Rate (kg/ha)} | | | | | | |
| | 1.0 % C | 1.0 % C | 1.0 % C | 0.5 % C | 2.0 % C | 2.0 % C | 8.0 % K |
| Cotton | 80 | 10 | 80 | 0 | 60 | 80 | 20 |
| Soybean | 100 | 90 | 100 | 30 | 80 | 80 | 100 |
| Field Corn | 100 | 100 | 100 | 80 | 100 | 100 | 100 |
| Rice | 100 | 95 | 100 | 80 | 90 | 90 | 100 |
| Wheat | 100 | 100 | 100 | 40 | 100 | 95 | 100 |
| Bindweed | 100 | 95 | 100 | 70 | 100 | 100 | 100 |
| Morningglory | 100 | 100 | 100 | 80 | 100 | 100 | 100 |
| Velvetleaf | 100 | 100 | 100 | 100 | 100 | 100 | 100 |
| Barnyardgrass | 100 | 100 | 100 | 95 | 100 | 100 | 100 |
| Green Foxtail | 100 | 100 | 100 | 100 | 100 | 100 | 100 |
| Johnsongrass | 100 | 100 | 100 | 95 | 100 | 100 | 100 |
| Yellow Nutsedge | — | — | — | — | — | — | 0 |

| | \multicolumn{7}{c}{Compound} | | | | | | |
|---|---|---|---|---|---|---|---|
| | 60 | 61 | 62 | 63 | 64 | 65 | 66 |
| | \multicolumn{7}{c}{Rate (kg/ha)} | | | | | | |
| | 8.0 | 1.0 | 0.5 | 0.5 | 2.0 | 1.0 | 0.5 |
| | % C | % C | % C | % C | % C | % C | % C |
| Cotton | 0 | 80 | 20 | 20 | 10 | 60 | 10 |
| Soybean | 10 | 95 | 90 | 80 | 95 | 30 | 10 |
| Field Corn | 0 | 100 | 100 | 100 | 100 | 80 | 90 |
| Rice | — | 100 | 80 | 90 | 100 | 80 | 100 |
| Wheat | 10 | 100 | 50 | 95 | 95 | 40 | 80 |
| Bindweed | 0 | 100 | — | 100 | 100 | 100 | 50 |
| Morningglory | 0 | 100 | 90 | 95 | 100 | 100 | 100 |
| Velvetleaf | 0 | 100 | 100 | 100 | 100 | 100 | 100 |
| Barnyardgrass | 0 | 100 | 100 | 100 | 100 | 100 | 95 |
| Green Foxtail | 0 | 100 | 100 | 100 | 100 | 95 | 40 |
| Johnsongrass | 0 | 100 | 95 | 100 | 100 | 100 | 90 |
| Yellow Nutsedge | — | — | 80 | — | — | — | — |

| | \multicolumn{7}{c}{Compound} | | | | | | |
|---|---|---|---|---|---|---|---|
| | 67 | 68 | 69 | 70 | 71 | 72 | 73 |
| | \multicolumn{7}{c}{Rate (kg/ha)} | | | | | | |
| | 1.0 % C | 8.0 % C | 1.0 % C | 1.0 % C | 1.0 % C | 1.0 % C | 1.0 % C |
| Cotton | 90 | 0 | 20 | 0 | 10 | 90 | 100 |
| Soybean | 70 | 0 | 20 | 10 | 0 | 100 | 100 |
| Field Corn | 70 | 0 | 80 | 10 | 70 | 100 | 100 |
| Rice | 60 | — | 50 | 0 | 40 | 100 | 100 |
| Wheat | 20 | 0 | 20 | 0 | 30 | 100 | 100 |
| Bindweed | 95 | 0 | 95 | 10 | 70 | 100 | 100 |
| Morningglory | 95 | 0 | 80 | 10 | 60 | 95 | 100 |
| Velvetleaf | 100 | 0 | 100 | 10 | 100 | 100 | 100 |
| Barnyardgrass | 100 | 0 | 95 | 10 | 100 | 100 | 100 |
| Green Foxtail | 90 | 0 | 100 | 0 | 95 | 100 | 100 |
| Johnsongrass | 90 | 0 | 95 | 10 | 90 | 100 | 100 |
| Yellow Nutsedge | — | — | — | — | — | — | — |

| | \multicolumn{7}{c}{Compound} | | | | | | |
|---|---|---|---|---|---|---|---|
| | 74 | 75 | 76 | 77 | 78 | 79 | 80 |
| | \multicolumn{7}{c}{Rate (kg/ha)} | | | | | | |
| | 1.0 % C | 2.0 % C | 0.5 % C | 1.0 % C | 1.0 % C | 1.0 % C | 1.0 % C |
| Cotton | 30 | 20 | 0 | 100 | 70 | 100 | 60 |
| Soybean | 100 | 30 | 20 | 100 | 95 | 100 | 90 |
| Field Corn | 100 | 90 | 20 | 100 | 100 | 100 | 100 |
| Rice | 100 | 30 | 40 | 100 | 100 | 100 | 95 |
| Wheat | 95 | 0 | 0 | 100 | 100 | 100 | 100 |
| Bindweed | 100 | 100 | 10 | 100 | 100 | 100 | 100 |
| Morningglory | 100 | 80 | 20 | 100 | 100 | 100 | 90 |
| Velvetleaf | 100 | 90 | 50 | 100 | 100 | 100 | 100 |
| Barnyardgrass | 100 | 90 | 60 | 100 | 100 | 100 | 60 |
| Green Foxtail | 100 | 90 | 0 | 100 | 100 | 100 | 100 |
| Johnsongrass | 100 | 60 | 30 | 100 | 100 | 100 | 80 |
| Yellow Nutsedge | — | 40 | — | — | — | — | — |

| | \multicolumn{4}{c}{Compound} | | | |
|---|---|---|---|---|
| | 81 | 82 | 83 | 84 |
| | \multicolumn{4}{c}{Rate (kg/ha)} | | | |
| | 1.0 % C | 1.0 % C | 1.0 % C | 1.0 % C |
| Cotton | 40 | 50 | 10 | 0 |
| Soybean | 70 | 95 | 30 | 40 |
| Field Corn | 100 | 100 | 90 | 95 |
| Rice | 95 | 100 | 90 | 90 |
| Wheat | 95 | 100 | 60 | 70 |
| Bindweed | 95 | 95 | 50 | 40 |
| Morningglory | 100 | 100 | 90 | 95 |
| Velvetleaf | 100 | 100 | 100 | 100 |
| Barnyardgrass | 100 | 100 | 100 | 100 |
| Green Foxtail | 100 | 100 | 90 | 100 |
| Johnsongrass | 100 | 100 | 100 | 100 |
| Yellow Nutsedge | — | — | — | — |

TABLE 4
POSTEMERGENCE HERBICIDAL ACTIVITY

| Compound |
|---|
| 1  2  3  5  6  7  8 |

TABLE 4-continued
POSTEMERGENCE HERBICIDAL ACTIVITY

| | \multicolumn{7}{c}{Rate (kg/ha)} | | | | | | |
|---|---|---|---|---|---|---|---|
| | 1.0 %C | 2.0 %C | 1.0 %C | 0.5 %C | 1.0 %C | 1.0 %C | 0.5 %C |
| Cotton | 80 | 80 | 100 | 100 | 80 | 95 | 100 |
| Soybean | 95 | 90 | 100 | 95 | 100 | 95 | 100 |
| Field Corn | 100 | 95 | 100 | 100 | 100 | 100 | 100 |
| Rice | 100 | 80 | 95 | 90 | 100 | 95 | 95 |
| Wheat | 100 | 90 | 95 | 95 | 100 | 80 | 95 |
| Bindweed | 80 | 95 | 100 | 100 | 100 | 100 | 10 |
| Morningglory | 100 | 100 | 100 | 100 | 100 | 100 | 100 |
| Velvetleaf | 95 | 100 | 100 | 100 | 100 | 100 | 100 |
| Barnyardgrass | 100 | 100 | 100 | 90 | 100 | 100 | 100 |
| Green Foxtail | 90 | 100 | 100 | 100 | 100 | 100 | 100 |
| Johnsongrass | 95 | 95 | 100 | 95 | 100 | 100 | 100 |
| Yellow Nutsedge | — | — | — | — | — | — | — |

| | \multicolumn{7}{c}{Compound} | | | | | | |
|---|---|---|---|---|---|---|---|
| | 9 | 10 | 11 | 12 | 13 | 14 | 15 |
| | \multicolumn{7}{c}{Rate (kg/ha)} | | | | | | |
| | 2.0 %C | 2.0 %C | 0.5 %C | 1.0 %C | 1.0 %C | 1.0 %C | 1.0 %C |
| Cotton | 80 | 100 | 100 | 100 | 90 | 50 | 80 |
| Soybean | 80 | 100 | 90 | 95 | 70 | 95 | 95 |
| Field Corn | 80 | 100 | 80 | 100 | 90 | 100 | 100 |
| Rice | 60 | 100 | 100 | 100 | 90 | 80 | 100 |
| Wheat | 70 | 100 | 90 | 100 | 90 | 100 | 100 |
| Bindweed | 100 | 100 | 90 | 100 | 95 | 100 | 90 |
| Morningglory | 90 | 100 | 100 | 100 | 90 | 100 | 100 |
| Velvetleaf | 100 | 100 | 100 | 100 | 100 | 100 | 100 |
| Barnyardgrass | 100 | 100 | 100 | 100 | 95 | 100 | 100 |
| Green Foxtail | 80 | 100 | 100 | 100 | 90 | 100 | 100 |
| Johnsongrass | 90 | 90 | 100 | 100 | 90 | 90 | 100 |
| Yellow Nutsedge | 20 | — | 50 | — | — | — | — |

| | \multicolumn{7}{c}{Compound} | | | | | | |
|---|---|---|---|---|---|---|---|
| | 16 | 17 | 18 | 19 | 20 | 21 | 22 |
| | \multicolumn{7}{c}{Rate (kg/ha)} | | | | | | |
| | 1.0 %C | 1.0 %C | 0.5 %C | 8.0 %C | 1.0 %C | 8.0 %K | 8.0 %K |
| Cotton | 100 | 100 | 90 | 10 | 100 | — | 80 |
| Soybean | 80 | 60 | 80 | 30 | 100 | 0 | 0 |
| Field Corn | 80 | 100 | 100 | 0 | 100 | 0 | 100 |
| Rice | 70 | 40 | 100 | — | — | — | 100 |
| Wheat | 30 | 80 | 100 | 0 | 100 | 0 | 100 |
| Bindweed | 70 | 70 | 100 | 0 | — | 0 | 100 |
| Morningglory | 100 | 80 | 100 | 0 | 100 | 0 | 100 |
| Velvetleaf | 100 | 100 | 100 | 10 | 100 | 0 | 100 |
| Barnyardgrass | 100 | 70 | 100 | — | 100 | 0 | 100 |
| Green Foxtail | 100 | 100 | 100 | 80 | 100 | 0 | 100 |
| Johnsongrass | 90 | 70 | 90 | 0 | 100 | 0 | 100 |
| Yellow Nutsedge | 0 | 0 | — | — | 90 | — | 0 |

| | \multicolumn{7}{c}{Compound} | | | | | | |
|---|---|---|---|---|---|---|---|
| | 23 | 24 | 25 | 26 | 27 | 28 | 29 |
| | \multicolumn{7}{c}{Rate (kg/ha)} | | | | | | |
| | 8.0 %C | 8.0 %K | 8.0 %K | 1.0 %C | 8.0 %K | 8.0 %K | 8.0 %K |
| Cotton | 0 | 100 | 100 | 100 | 90 | 60 | 0 |
| Soybean | 0 | 10 | 20 | 80 | 20 | 0 | 0 |
| Field Corn | 0 | 100 | 60 | 50 | 70 | 100 | 60 |
| Rice | — | 90 | 0 | 50 | 20 | 0 | 40 |
| Wheat | 0 | 100 | 0 | 20 | 10 | 80 | 0 |
| Bindweed | 0 | 100 | 80 | 80 | 100 | 80 | 100 |
| Morningglory | 0 | 100 | 100 | 90 | 90 | 100 | 40 |
| Velvetleaf | 0 | 100 | 100 | 100 | 100 | 100 | 100 |
| Barnyardgrass | — | 100 | 50 | 30 | 10 | 100 | 30 |
| Green Foxtail | 0 | 100 | 90 | 90 | 20 | 100 | 100 |
| Johnsongrass | 0 | 100 | 95 | 80 | 100 | 100 | 60 |
| Yellow Nutsedge | — | 0 | 0 | 20 | 0 | 0 | 0 |

| | \multicolumn{7}{c}{Compound} | | | | | | |
|---|---|---|---|---|---|---|---|
| | 30 | 31 | 32 | 34 | 35 | 36 | 37 |
| | \multicolumn{7}{c}{Rate (kg/ha)} | | | | | | |
| | 8.0 %K | 8.0 %K | 4.0 %C | 8.0 %C | 1.0 %C | 1.0 %C | 1.0 %C |
| Cotton | 0 | 80 | 70 | 20 | 20 | 50 | 40 |
| Soybean | 0 | 0 | 30 | 70 | 80 | 80 | 70 |
| Field Corn | 0 | 100 | 0 | 10 | 60 | 30 | 30 |
| Rice | — | 10 | 10 | — | 10 | 20 | 20 |
| Wheat | 0 | 90 | 10 | 10 | 10 | 30 | 40 |
| Bindweed | 0 | 90 | 90 | 20 | 20 | 30 | 40 |
| Morningglory | 0 | 20 | 50 | 10 | 90 | 80 | 80 |
| Velvetleaf | 0 | 100 | 100 | 20 | 100 | 100 | 100 |
| Barnyardgrass | 0 | 40 | 0 | 10 | 90 | 40 | 70 |
| Green Foxtail | 0 | 100 | 100 | 60 | 30 | 60 | 100 |
| Johnsongrass | 0 | 100 | 90 | 10 | 80 | 30 | 60 |
| Yellow Nutsedge | — | 0 | 0 | — | — | — | — |

| | \multicolumn{7}{c}{Compound} | | | | | | |
|---|---|---|---|---|---|---|---|
| | 38 | 39 | 40 | 41 | 42 | 43 | 45 |
| | \multicolumn{7}{c}{Rate (kg/ha)} | | | | | | |
| | 1.0 %C | 8.0 %C | 2.0 %C | 8.0 %K | 8.0 %K | 8.0 %K | 1.0 %C |
| Cotton | 80 | 20 | 70 | 20 | 100 | 90 | 70 |
| Soybean | 70 | 10 | 40 | 0 | 100 | 0 | 70 |
| Field Corn | 80 | 20 | 10 | 0 | 100 | 60 | 80 |
| Rice | 60 | 0 | 20 | 0 | 95 | 0 | 50 |
| Wheat | 60 | 10 | 20 | 0 | 100 | 20 | 30 |
| Bindweed | 60 | 10 | 60 | 30 | 100 | 0 | 30 |
| Morningglory | 100 | 20 | 40 | 20 | 100 | 90 | 95 |
| Velvetleaf | 100 | 0 | 90 | 100 | 100 | 100 | 100 |
| Barnyardgrass | 80 | 40 | 20 | 0 | 100 | 0 | 50 |
| Green Foxtail | 90 | 10 | 80 | 95 | 100 | 60 | 90 |
| Johnsongrass | 60 | 30 | 30 | 0 | 100 | 100 | 60 |
| Yellow Nutsedge | — | 20 | 20 | 0 | 70 | 0 | — |

| | \multicolumn{7}{c}{Compound} | | | | | | |
|---|---|---|---|---|---|---|---|
| | 46 | 47 | 48 | 49 | 50 | 51 | 52 |
| | \multicolumn{7}{c}{Rate (kg/ha)} | | | | | | |
| | 8.0 %C | 2.0 %C | 8.0 %C | 8.0 %C | 2.0 %C | 1.0 %C | 1.0 %C |
| Cotton | 50 | 50 | 50 | 90 | 10 | 90 | 50 |
| Soybean | 60 | 70 | 40 | 50 | 90 | 100 | 95 |
| Field Corn | 70 | 95 | 30 | 60 | 50 | 100 | 100 |
| Rice | 50 | 30 | — | 70 | 95 | 100 | 100 |
| Wheat | 20 | 100 | 40 | 10 | 50 | 95 | 100 |
| Bindweed | 100 | 95 | 90 | 70 | 100 | 100 | 100 |
| Morningglory | 95 | 90 | 60 | 100 | 100 | 100 | 95 |
| Velvetleaf | 100 | 100 | 80 | 100 | 100 | 100 | 100 |
| Barnyardgrass | 95 | 80 | 50 | 90 | 100 | 100 | 100 |
| Green Foxtail | 50 | 80 | 40 | 40 | 80 | 100 | 95 |
| Johnsongrass | 70 | 80 | 50 | 70 | 95 | 90 | 80 |
| Yellow Nutsedge | — | — | — | — | — | — | — |

| | \multicolumn{7}{c}{Compound} | | | | | | |
|---|---|---|---|---|---|---|---|
| | 53 | 54 | 55 | 56 | 57 | 58 | 59 |
| | \multicolumn{7}{c}{Rate (kg/ha)} | | | | | | |
| | 1.0 %C | 1.0 %C | 1.0 %C | 0.5 %C | 2.0 %C | 2.0 %C | 8.0 %K |
| Cotton | 100 | 95 | 100 | 100 | 40 | 80 | 100 |
| Soybean | 100 | 95 | 100 | 40 | 95 | 95 | 30 |
| Field Corn | 100 | 100 | 100 | 70 | 100 | 100 | 100 |
| Rice | 100 | 100 | 95 | 80 | 95 | 95 | 100 |
| Wheat | 100 | 95 | 100 | 10 | 100 | 100 | 100 |
| Bindweed | 100 | 100 | 100 | 80 | 95 | 100 | 100 |
| Morningglory | 100 | 100 | 100 | 90 | 100 | 100 | 100 |
| Velvetleaf | 100 | 100 | 100 | 95 | 100 | 100 | 100 |
| Barnyardgrass | 100 | 100 | 100 | 90 | 100 | 100 | 100 |
| Green Foxtail | 100 | 100 | 100 | 70 | 100 | 100 | 100 |
| Johnsongrass | 90 | 100 | 95 | 80 | 100 | 100 | 100 |
| Yellow Nutsedge | — | — | — | — | — | — | 40 |

| | \multicolumn{7}{c}{Compound} | | | | | | |
|---|---|---|---|---|---|---|---|
| | 60 | 61 | 62 | 63 | 64 | 65 | 66 |
| | \multicolumn{7}{c}{Rate (kg/ha)} | | | | | | |
| | 8.0 %C | 1.0 %C | 0.5 %C | 0.5 %C | 2.0 %C | 1.0 %C | 0.5 %C |
| Cotton | 20 | 80 | 100 | 100 | 40 | 0 | 30 |
| Soybean | 40 | 95 | 95 | 95 | 95 | 70 | 60 |
| Field Corn | 30 | 100 | 100 | 100 | 60 | 60 | 30 |
| Rice | — | 95 | 90 | 100 | 95 | 70 | 95 |
| Wheat | 10 | 90 | 80 | 70 | 30 | 40 | 30 |
| Bindweed | 10 | 100 | 100 | 40 | 100 | 60 | 20 |
| Morningglory | 0 | 100 | 100 | 100 | 100 | 100 | 100 |
| Velvetleaf | 0 | 100 | 100 | 100 | 100 | 100 | 100 |
| Barnyardgrass | 30 | 95 | 100 | 90 | 100 | 95 | 90 |

TABLE 4-continued
POSTEMERGENCE HERBICIDAL ACTIVITY

| | | | | | | | |
|---|---|---|---|---|---|---|---|
| Green Foxtail | 20 | 100 | 100 | 95 | 100 | 90 | 70 |
| Johnsongrass | 10 | 90 | 90 | 90 | 100 | 80 | 80 |
| Yellow Nutsedge | — | — | — | — | — | — | — |

| | Compound | | | | | | |
|---|---|---|---|---|---|---|---|
| | 67 | 68 | 69 | 70 | 71 | 72 | 73 |
| | Rate (kg/ha) | | | | | | |
| | 1.0 | 8.0 | 1.0 | 1.0 | 1.0 | 1.0 | 1.0 |
| | % C | % C | % C | % C | % C | % C | % C |
| Cotton | 100 | 40 | 90 | 10 | 100 | 95 | 100 |
| Soybean | 100 | 20 | 70 | 10 | 90 | 100 | 100 |
| Field Corn | 100 | 20 | 80 | 10 | 100 | 100 | 100 |
| Rice | 90 | — | 50 | 10 | 70 | 100 | 100 |
| Wheat | 90 | 0 | 40 | 10 | 70 | 100 | 100 |
| Bindweed | 100 | 20 | 100 | 30 | 90 | 100 | 100 |
| Morningglory | 100 | 30 | 95 | 10 | 95 | 100 | 100 |
| Velvetleaf | 100 | 70 | 100 | 10 | 100 | 100 | 100 |
| Barnyardgrass | 100 | 30 | 95 | 20 | 95 | 100 | 100 |
| Green Foxtail | 100 | 30 | 100 | 20 | 80 | 90 | 100 |
| Johnsongrass | 100 | 30 | 95 | 30 | 95 | 95 | 90 |
| Yellow Nutsedge | — | — | — | — | — | — | — |

| | Compound | | | | | | |
|---|---|---|---|---|---|---|---|
| | 74 | 75 | 76 | 77 | 78 | 79 | 80 |
| | Rate (kg/ha) | | | | | | |
| | 1.0 | 2.0 | 0.5 | 1.0 | 1.0 | 1.0 | 1.0 |
| | % C | % C | % C | % C | % C | % C | % C |
| Cotton | 50 | 100 | 50 | 95 | 40 | 90 | 10 |
| Soybean | 100 | 50 | 50 | 100 | 100 | 100 | 90 |
| Field Corn | 100 | 50 | 30 | 100 | 95 | 100 | 90 |
| Rice | 90 | 80 | 40 | 100 | 80 | 100 | 40 |
| Wheat | 60 | 50 | 20 | 95 | 80 | 100 | 70 |
| Bindweed | 100 | 90 | 40 | 100 | 80 | 80 | 60 |
| Morningglory | 100 | 90 | 80 | 100 | 100 | 100 | 80 |
| Velvetleaf | 100 | 100 | 90 | 100 | 90 | 80 | 60 |
| Barnyardgrass | 80 | 40 | 20 | 95 | 80 | 95 | 50 |
| Green Foxtail | 95 | 80 | 50 | 95 | 80 | 100 | 70 |
| Johnsongrass | 70 | 30 | 60 | 80 | 70 | 95 | 60 |
| Yellow Nutsedge | — | 0 | — | — | — | — | — |

| | Compound | | | | |
|---|---|---|---|---|---|
| | 81 | 82 | | 83 | 84 |
| | Rate (kg/ha) | | | | |
| | 1.0 | 1.0 | | 1.0 | 1.0 |
| | % C | % C | | % C | % C |
| Cotton | 60 | 95 | | 20 | 50 |
| Soybean | 95 | 100 | | 90 | 70 |
| Field Corn | 80 | 100 | | 90 | 90 |
| Rice | 70 | 100 | | 60 | 30 |
| Wheat | 70 | 100 | | 80 | 40 |
| Bindweed | 95 | 100 | | 95 | 10 |
| Morningglory | 100 | 100 | | 100 | 80 |
| Velvetleaf | 100 | 100 | | 100 | 70 |
| Barnyardgrass | 100 | 100 | | 100 | 100 |
| Green Foxtail | 100 | 100 | | 100 | 70 |
| Johnsongrass | 100 | 100 | | 100 | 80 |
| Yellow Nutsedge | — | — | | — | — |

I claim:

1. A hebicidal compound having the formula

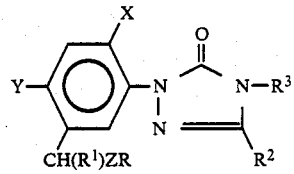

in which Z is O or $SO_n$ and n is zero, one or two; R is hydrogen, alkyl, haolalkyl, cycloalkyl having 3-6 carbon atoms in the ring, alkenyl, alkynl, alkoxyalkyl, C4-5 cyclic oxyalkylene, alkylcarbonyl, haloalkylcarbonyl, alkyloxycarbonylalkyl, phenoxycarbonylalkyl, halophenoxycarbonylalkyl, alkoxyphenoxycarbonylalkyl, alkylphenoxycarbonylalkyl, haloalkylphenoxycarbonylalkyl, nitro, phenyl, halophenyl, alkoxyphenyl, alkylphenyl, haloalkylphenyl, benzyl, or cyano; Rhu 1 is hydrogen, lower alkyl or haloalkyl; $R^2$ is halogen, lower alkyl or lower haloalkyl; $R^3$ is lower alkyl or haloalkyl; X is hydrogen, hydrogen alkyl, haloalkyl, alkoxy or nitro; Y is hydrogen, halogen, alkyl, alkoxy, haloalkyl, halo lower alkylsulfinyl or halo lower alkoxy and wherein any alkyl, alkenyl, alkynyl or alkylene moiety has less than 6 carbon atoms.

2. A compound as in claim 1 in which $R^2$ is $CH_3$, $R^3$ is $CHF_2$, X is F or Cl, and Y is Cl or Br.

3. A herbicidal composition comprising a herbicidally effective amount of the compound of claim 1 in admixture with a suitable carrier.

4. A method for controlling undesired plant growth which comprises applying to the locus where control is desired a herbicidally effective amount of the composition of claim 3.

* * * * *